United States Patent
Lindner et al.

(10) Patent No.: US 11,673,260 B2
(45) Date of Patent: Jun. 13, 2023

(54) SYSTEMS AND METHODS FOR GRIPPING CYLINDRICAL OBJECTS IN A MANUFACTURING ENVIRONMENT

(71) Applicant: ATS AUTOMATION TOOLING SYSTEMS INC., Cambridge (CA)

(72) Inventors: Roland Lindner, Winnenden (DE); Ralph Rosenkranz, Winnenden (DE)

(73) Assignee: ATS CORPORATION, Cambridge (CA)

( * ) Notice: Subject to any disclaimer, the term of this patent is extended or adjusted under 35 U.S.C. 154(b) by 0 days.

(21) Appl. No.: 17/217,529

(22) Filed: Mar. 30, 2021

(65) Prior Publication Data
US 2021/0299887 A1    Sep. 30, 2021

Related U.S. Application Data

(60) Provisional application No. 63/002,856, filed on Mar. 31, 2020.

(51) Int. Cl.
*B25J 9/10* (2006.01)
*B25J 15/00* (2006.01)
*B25J 15/02* (2006.01)

(52) U.S. Cl.
CPC .......... *B25J 9/109* (2013.01); *B25J 15/0028* (2013.01); *B25J 15/0042* (2013.01);
(Continued)

(58) Field of Classification Search
CPC .... B25J 15/0028; B25J 9/109; B25J 15/0042; B65B 21/12; B65G 2201/0244; B65G 47/842
(Continued)

(56) References Cited

U.S. PATENT DOCUMENTS 3,108,835 A  *  10/1963  Rowekamp ............. B65B 21/12
                                                    294/90
4,034,542 A  *   7/1977  Loehr ................. A01D 46/247
                                                    294/111
(Continued)

FOREIGN PATENT DOCUMENTS

CN    109318250 A    2/2019
CN    209478222 U    10/2019
(Continued)

OTHER PUBLICATIONS

European Search Report on corresponding EP Pat. App. No. 21165861.2, European Patent Office, dated Nov. 30, 2021.
(Continued)

*Primary Examiner* — Gregory W Adams
(74) *Attorney, Agent, or Firm* — Amarok IP Inc.; Neil W. Henderson

(57) ABSTRACT

A system and method for gripping a cylindrical object. The system including: a housing; a plurality of gripping arms in the housing, the gripping arms in pairs each on an opposite side of a centerline plane from another; and a driving wedge in the housing and configured such that movement of the driving wedge moves each pair of gripping arms towards or away from each other while remaining equidistant from the centerline plane. The method including: opening the plurality of gripping arms against a bias by sliding a wedge in a first direction to slide the plurality of gripping arms apart while maintaining an equal predetermined distance from a part alignment position; placing a cylindrical body between the plurality of gripping arms; and closing the plurality of gripping arms by sliding the wedge in an opposite direction to allow the biasing force to close the gripping arms.

14 Claims, 20 Drawing Sheets

(52) U.S. Cl.
CPC ......... *B25J 15/0052* (2013.01); *B25J 15/028* (2013.01); *B25J 15/0226* (2013.01)

(58) Field of Classification Search
USPC ....... 198/468.2, 803.7, 867.05; 294/115, 116
See application file for complete search history.

(56) References Cited

U.S. PATENT DOCUMENTS

| | | | | |
|---|---|---|---|---|
| 5,277,689 | A * | 1/1994 | Ruetschle | B25J 15/0206 |
| | | | | 483/902 |
| 5,471,738 | A | 12/1995 | Burcham et al. | |
| 5,762,391 | A | 6/1998 | Sumnitsch | |
| 9,732,568 | B2 * | 8/2017 | Lindberg | E21B 19/087 |
| 2016/0154017 | A1 * | 6/2016 | Oguri | G01N 35/025 |
| | | | | 294/203 |
| 2021/0299887 | A1 | 9/2021 | Lindner et al. | |

FOREIGN PATENT DOCUMENTS

| | | | |
|---|---|---|---|
| DE | 3322142 A1 | 12/1984 | |
| DE | 112006000620 T5 * | 2/2008 | .......... B25J 15/0052 |
| KR | 101026042 B1 | 3/2011 | |

OTHER PUBLICATIONS

European Patent Office, Examiner's Report on corresponding EP Pat. App. No. 21165861.2, dated Nov. 4, 2022.

* cited by examiner

SYSTEMS AND METHODS FOR GRIPPING CYLINDRICAL OBJECTS IN A MANUFACTURING ENVIRONMENT

CROSS-REFERENCE TO OTHER APPLICATIONS

This document claims priority from U.S. Provisional Application No. 63/002,856 filed Mar. 31, 2020, which is hereby incorporated herein by reference.

FIELD

This document relates generally to systems and methods for gripping cylindrical objects in a manufacturing environment and, more particularly, to a system and method for gripping syringe bodies during manufacturing of the syringe.

BACKGROUND

Automated manufacturing processes typically require parts to be releasably gripped in careful alignment relative to one another prior to assembly into a product. Conventional gripping mechanisms are designed to grip a part having particular dimensions within particular tolerances, and cannot be used with parts having differing dimensions. However, a production line using automated manufacturing may need to change the dimensions of one or more parts from time to time, for example when a product line includes products having a range of sizes. This requires re-tooling of the production line to exchange the gripping mechanisms to accommodate the change in part dimensions, typically causing significant downtime on the production line.

Cylindrical parts may require careful alignment with the centerline of the cylinder, for example to align a syringe cannula with a syringe body, and pose a particular challenge with regard to accommodating changes in dimensions. Cylindrical parts are typically gripped by their outer edges, however a change in diameter causes a change in the position of the centerline of the cylinder relative to the edge of the cylinder. Cylindrical parts typically require a specific offset in the gripping mechanism to accommodate each size of cylinder used, causing downtime when the part sizes are changed. There is therefore an unmet need in the art for a gripping mechanism that can grip cylindrical parts of varying sizes while maintaining a constant position of the centerline of the part.

SUMMARY

According to an aspect herein there is provided a system for gripping a cylindrical object, the system including: a housing; a plurality of gripping arms provided to the housing, the plurality of gripping arms arranged in pairs with one gripping arm on an opposite side of a centerline plane from another gripping arm; and a driving wedge mounted in the housing and configured such that movement of the driving wedge moves each pair of gripping arms towards or away from each other such that each of the pair of gripping arms remains equidistant from the centerline plane.

In some cases, each of the plurality of gripping arms may be biased toward the centerline plane and the driving wedge may be configured to move each pair of gripping arms away from the centerline plane.

In some cases, each of the plurality of gripping arms may be biased away from the centerline plane and the driving wedge may be configured to move each pair of gripping arms toward the centerline plane.

In some cases, each of the plurality of gripping arms may include a driven surface and the driving wedge may include at least one driving surface configured to match with the driven surface to move the gripping arm.

In these cases, each of the plurality of gripping arms may further include: a connecting portion having a first end and a second end opposite the first end; a gripping portion positioned at the first end; and the driven surface positioned at the second end.

Also in these cases, each of the plurality of gripping arms may include an additional driven surface symmetrical with the first driven surface across a mirror plane of symmetry perpendicular to the first direction.

Still further, in these cases, each driven surface and driving surface may be configured at complementary driving angles with respect to the centerline plane. In some cases, the driving angle may be between 5 and 25 degrees.

In some cases, the system may further include a cam, wherein the driving wedge is moveable in response to movement of the cam and the driving wedge is biased away from the plurality of gripping arms.

According to another aspect herein, there is provided a method for actuating a gripper for a cylindrical object, the method including: configuring the gripper to be closed based on a biasing force on a plurality of gripping arms; opening the plurality of gripping arms against the bias by sliding a wedge in a first direction to slide against a corresponding one of the plurality of gripping arms such that each of the gripping arms maintain an equal predetermined distance from a part alignment position; placing a cylindrical body between the plurality of gripping arms; and closing the plurality of gripping arms by sliding the wedge in an opposite direction to allow the biasing force to close the gripping arms and allow the gripping arms to grip the cylindrical body in alignment with the part alignment position.

In some cases, the wedge may include at lease one driving surface and each gripping arm may include at least one driven surface corresponding to the driving surface, and wherein opening the gripping arms includes moving each gripping arm in response to contact between the driving surface and the corresponding driven surface. Similarly, the closing the gripping arms may include moving each gripping arm in response to a reduced contact between the driving surface and the corresponding driven surface aided by the biasing force.

In some cases, the method may further include opening the plurality of gripper arms to release the cylindrical body from the plurality of gripping arms.

According to another aspect herein, there is provided a system for gripping a cylindrical object, the system including: a housing; a driving wedge mounted in the housing and slidable in a first direction (Z), the first direction (Z) aligned with a first plane (Y-Z) passing through a part alignment position, the driving wedge including a plurality of driving surfaces positioned symmetrically and at a driving angle relative to the first (Z) direction; and a plurality of gripping arms mounted in the housing and movable in at least a second (X) direction, each of the plurality of gripping arms including one of a plurality of driven surfaces complementary to one of the plurality of driving surfaces, each of the plurality of gripping arms positioned such that contact between the plurality of driving surfaces and the plurality of driven surfaces causes the plurality of gripping arms to move in at least the second (X) direction in response to movement of the driving wedge in the first direction.

In some cases, the gripping system may further include: at least one additional driving wedge mounted in the housing and slidable in an additional first (Z) direction, the additional first direction (Z) aligned with an additional first plane (Y-Z) passing through an additional part alignment position, each additional driving wedge including an additional plurality of driving surfaces positioned symmetrically and at an additional driving angle relative to the additional first (Z) direction; and at least one additional plurality of gripping arms mounted in the housing and movable in at least an additional second (X) direction, each of the additional plurality of gripping arms including one of an additional plurality of driven surfaces complementary to one of the additional plurality of driving surfaces, each of the additional plurality of gripping arms positioned such that contact between the additional plurality of driving surfaces and the additional plurality of driven surfaces causes the additional plurality of gripping arms to move in at least the additional second (X) direction in response to movement of the additional driving wedge in the additional first direction.

DETAILED DESCRIPTION

Various systems, apparatuses or methods will be described herein to provide example embodiment(s). No embodiment described below is intended to limit any claimed invention. The claims are not limited to systems, apparatuses or methods having all of the features of any one embodiment or to features common to multiple or all of the embodiments described herein. A claim may include features taken from any embodiment or a selection of embodiments as would be understood by one of skill in the art. The applicants, inventors or owners reserve all rights that they may have in any invention disclosed herein, for example the right to claim such an invention in a continuing application and do not intend to abandon, disclaim or dedicate to the public any such invention by its disclosure in this document.

The present disclosure relates generally to an actuated gripper for holding one or more syringe barrels, or more generally, cylindrical bodies. The gripper may accommodate syringe barrels made of varying materials, for example glass, plastic, metal, or other materials. Furthermore, the gripper may accommodate cylindrical bodies that are not syringe bodies. The gripper may accommodate different diameters of syringe barrels, including diameters defined by standard sizes and can be actuated to grip and/or release syringe barrels in such a way that a center axis (sometimes referred to as a centerline) of each of the syringe barrels is in a predetermined position. In this way, the gripper is intended to accommodate variations in barrel diameter. For syringe barrels there may be significant variation in barrel diameter from one type of barrel to the next. In some cases, there may be variation in barrel diameter from one part to the next, owing to the material characteristics and manufacturing processes of the syringe barrel or parts. In some embodiments, the syringe barrels may be positioned vertically within the grippers such that a pre-determined length of the syringe body (e.g. a dome or the like) extends above/out of the gripper.

Figure 1:
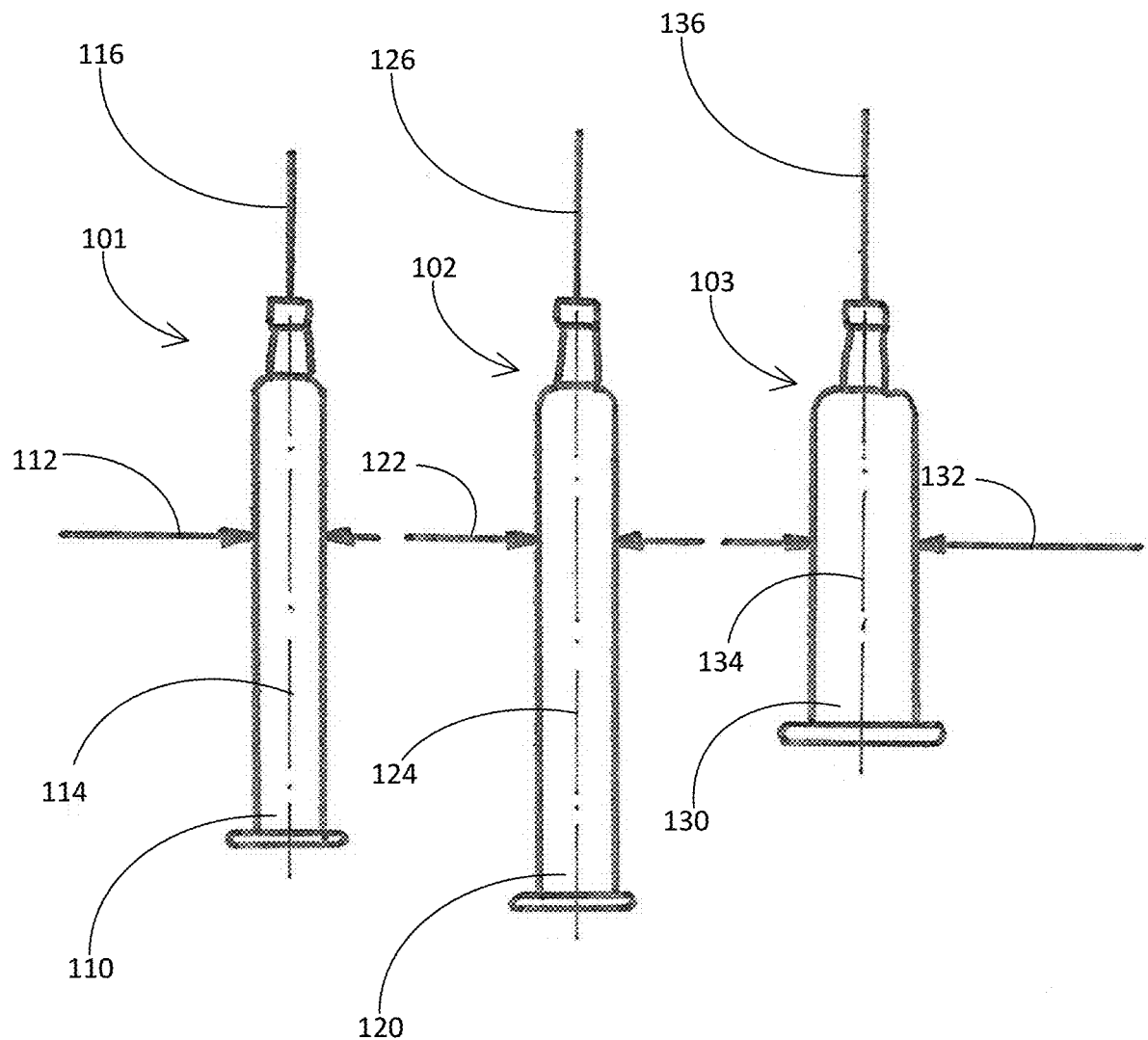
FIG. 1 shows a schematic view of three exemplary syringes.

FIG. 1 shows a side view of three exemplary syringes 101, 102, and 103 of a type that can be gripped by embodiments of the system and method disclosed herein. Each syringe typically includes a plunger, a barrel, and a needle. Syringes 101, 102, and 103 include syringe barrels 110, 120, and 130, having diameters 112, 122, and 132, and centerlines 114, 124, and 134, and needles 116, 126, and 136, respectively. Plungers are not shown. In the context of the present disclosure, the term "needle" includes both needles and cannulae, where a needle typically has a sharp tip while a cannula typically has a blunt tip. Automated assembly of syringes may include inserting a needle into an end of a syringe barrel and, generally speaking, the needle and the centerline of the syringe barrel need to be aligned. The needle may then be affixed to the syringe barrel, for example with glue or the like. While needles 116, 126, and 136 may have different gauges and lengths, a portion of each needle will be affixed in respective syringe barrels within manufacturing tolerances.

It is desirable to have the centerline of the syringe barrel in the same position, independent of the size of the syringe, as this avoids the need to change the position at which the needle is inserted into the syringe barrel. As illustrated in FIG. 1, the diameters 112, 122, and 132 may be different from one another which, in conventional manufacturing, can shift the positions of centerlines 114, 124, and 134 relative to exterior gripping surfaces of syringe barrels 110, 120 and 130. For example, diameter 112 may be approximately 7 mm, diameter 122 may be approximately 8 mm, and diameter 132 may be approximately 10 mm. For conventional grippers, assembling syringes 101 and then assembling syringes 102 may require a resetting/reprogramming or other change to the production line. To avoid the need to take these additional steps, a gripper according to embodiments herein is configured to hold the syringe barrel in a manner such that the position of the centerline of the syringe barrel is unaffected by the size/diameter of the syringe barrel.

Figure 2A:
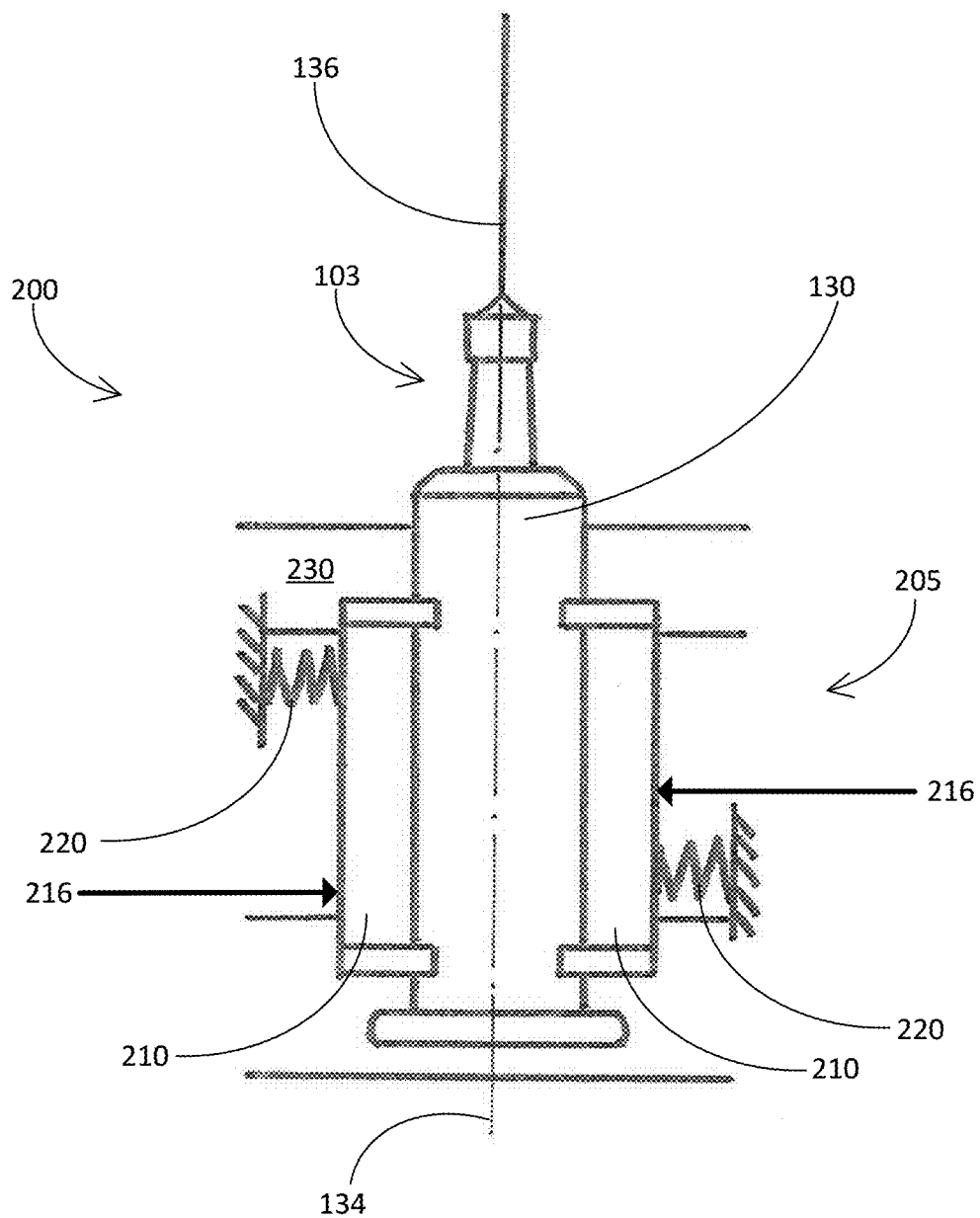
FIG. 2A is a front view of a gripper biased to grip a cylindrical body according to an embodiment herein.
Figure 2B:
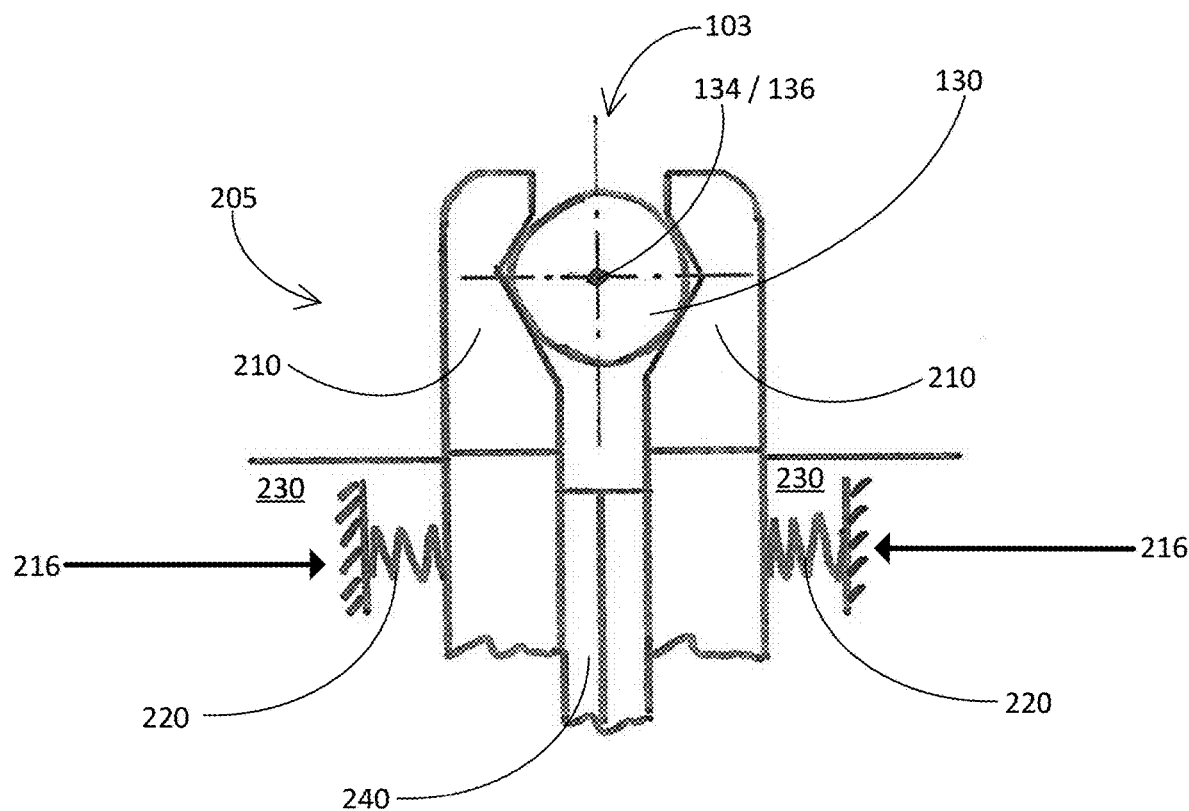
FIG. 2B is a top view of a gripper biased to grip a cylindrical body the embodiment of FIG. 2A.

FIG. 2A is a front view of a system 200 in which a gripper 205 is biased to grip a cylindrical body 130 according to an embodiment herein. FIG. 2B is a top view of the gripper 205. The system 200 includes the gripper 205 (including two gripping arms 210, two springs 220), a housing 230, and a driving wedge 240 (illustrated partially in FIG. 2B and shown in further detail in later figures). The driving wedge 240 is mounted in the housing 230 and is slideable in a first direction (referred to as the Z direction herein). A skilled person, with the benefit of the present disclosure, will appreciate that when an element (e.g. a driving wedge, a gripping arm) is referred to as slidable and/or movable in a given direction, the element may also be slidable and/or movable in a direction opposite the given direction. Each gripping arm 210 is slideably mounted in the housing 230 and is slideable in a second direction, (left and right in FIGS. 2A and 2B, for example the X direction, which is generally perpendicular to the first direction (Z direction)). The two gripping arms 210 may be moved together to grip a cylindrical body and/or moved apart to release a cylindrical body. A skilled person, with the benefit of the present disclosure, will appreciate that in other embodiments the gripping arms may alternatively be pivotably mounted in the housing.

Each spring 220 exerts a bias force 216 on each gripping arm 210, causing each gripping arm to be biased to a closed position and thus, contact opposite sides of syringe barrel 130 when present. Each bias force 216 may be, for example, between 5 and 35 Newtons to grip cylindrical bodies made of relatively rigid/strong materials, for example syringe bodies made of glass, plastic, metal or the like. For cylindrical bodies made of lower strength/less rigid materials, for example, elastomers, or the like, a reduced gripping force may be employed. The bias force 216 is thereby exerted on the syringe barrel 130, and the resulting friction between each gripping arm 210 and the syringe barrel 130 causes the two gripping arms 210 to grip the syringe barrel 130. It will be understood that the bias force 216 should, in any event, be less than the breaking point of the syringe barrel 130. In some embodiments, the bias force 216 may be less than e.g. 10 N.

Each gripping arm 210 is positioned an equal distance from a centerline 134 of the syringe and biased toward that centerline, and syringe centerline 134 is aligned with needle 136 and/or the mechanism that provides needle 136. In the present embodiment, the position of needle 136 is a position that centerline 134 must be aligned with prior to inserting needle 136 into syringe barrel 130. In other words, the position of needle 136 is a part alignment position, and syringe barrel 130 is aligned with the part alignment position. As will be explained below, if syringe 101 was gripped by gripper 200 instead of syringe 103, centerline 114 would remain aligned with the part alignment position.

Figure 3A:
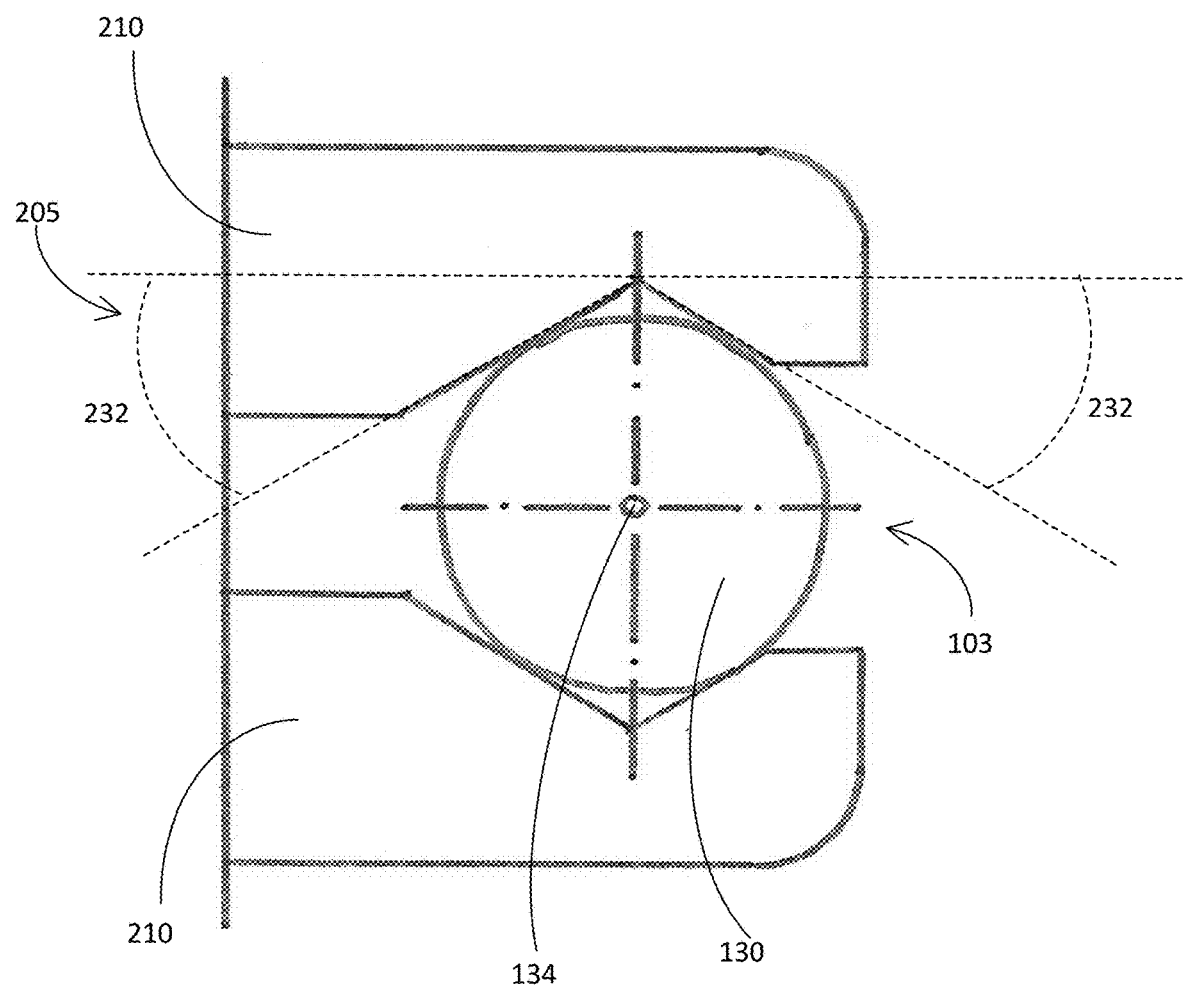
FIG. 3A is a top view of a portion of gripper biased to grip the cylindrical body according to an embodiment herein.
Figure 3B:
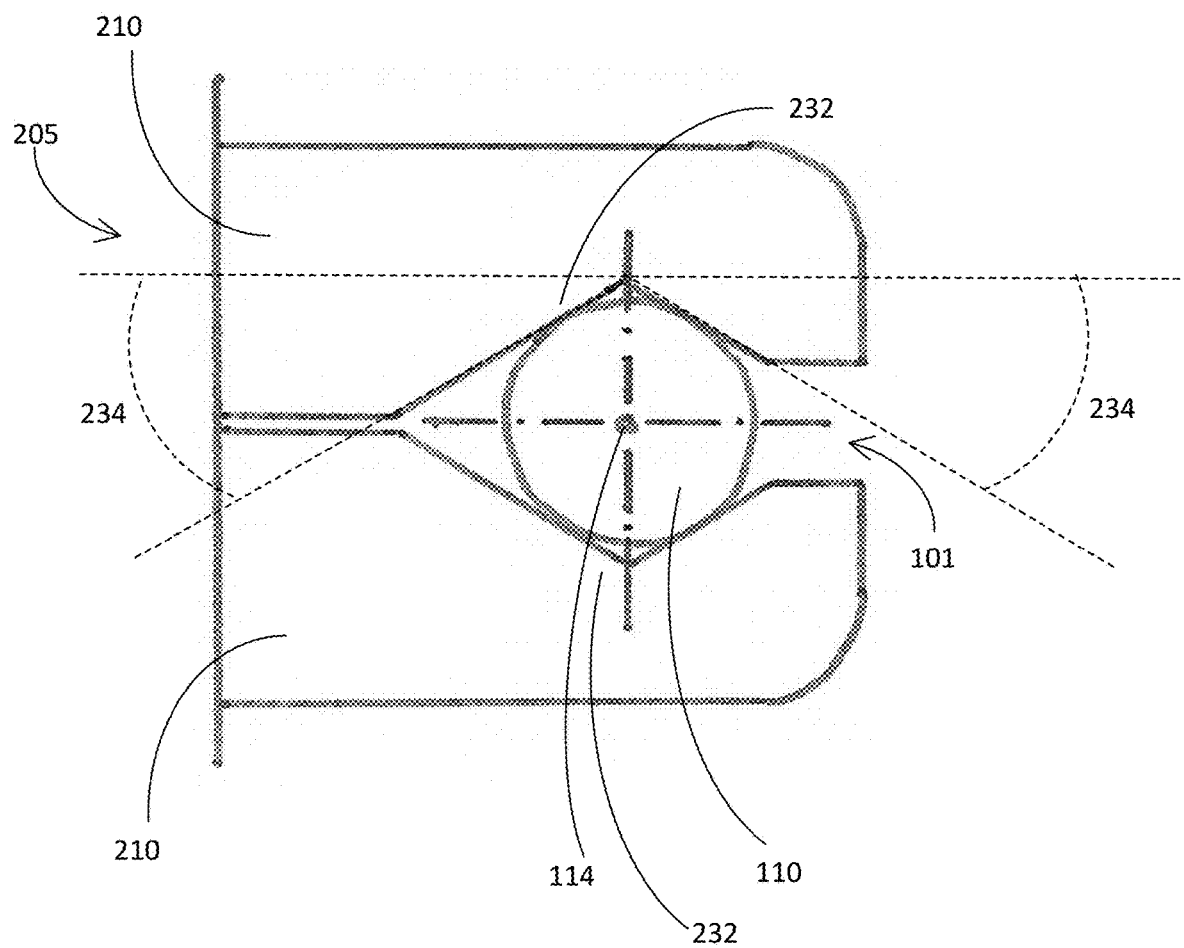
FIG. 3B is a top view of a portion of gripper biased to grip the cylindrical body according to an embodiment herein.

FIG. 3A is a top view of a portion of gripper 205 biased to grip the cylindrical body 130 according to an embodiment herein. FIG. 3B is a top view of a portion of gripper 205 biased to grip the cylindrical body 110 according to an embodiment herein. In FIG. 3B, both gripping arms 210 are closer together to grip cylindrical body 110 compared to the positions of both gripping arms 210 in FIG. 3A. In particular, each gripping arm 210 is positioned an equal distance closer to the part alignment position in FIG. 3B compared to FIG. 3A, with the gripping arms 210 remaining parallel to one another. The parallel movement of the gripping arms 210 allows the gripping arms 210 to grip cylindrical bodies of varying diameters without changing the position of the centerline of each cylindrical body relative to the gripper 205. Each gripping arm 210 includes a jaw 232. Each jaw 232 is formed of two surfaces formed at an angle, with a meeting point of the angles aligned with the part alignment position. The angle 234 of the surfaces relative to a line perpendicular to the direction of movement is shown in FIGS. 3A and 3B may be between 20 and 40 degrees.

Figure 4A:
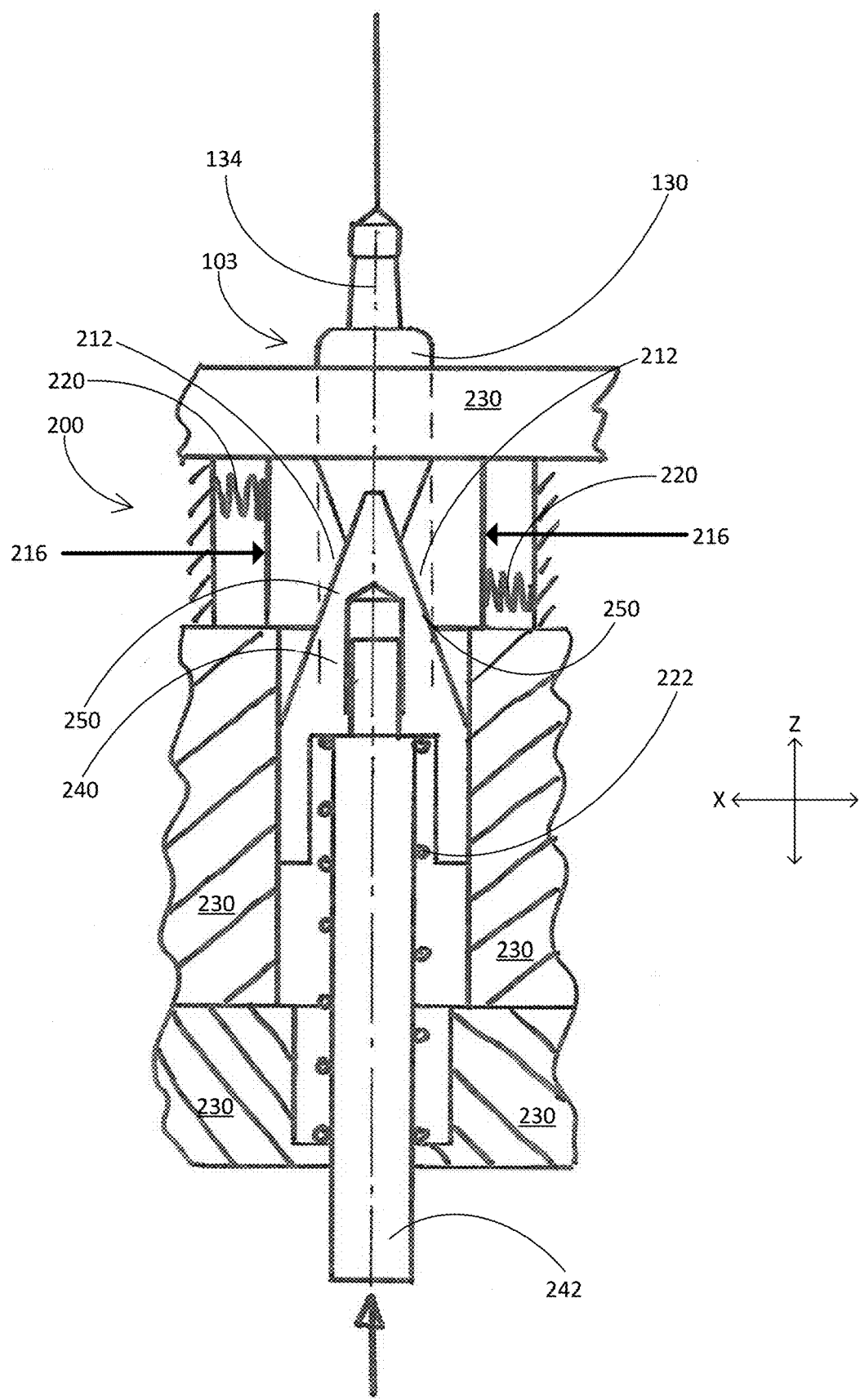
FIG. 4A is a cutaway rear view of gripper biased to grip the cylindrical body according to an embodiment herein.
Figure 4B:
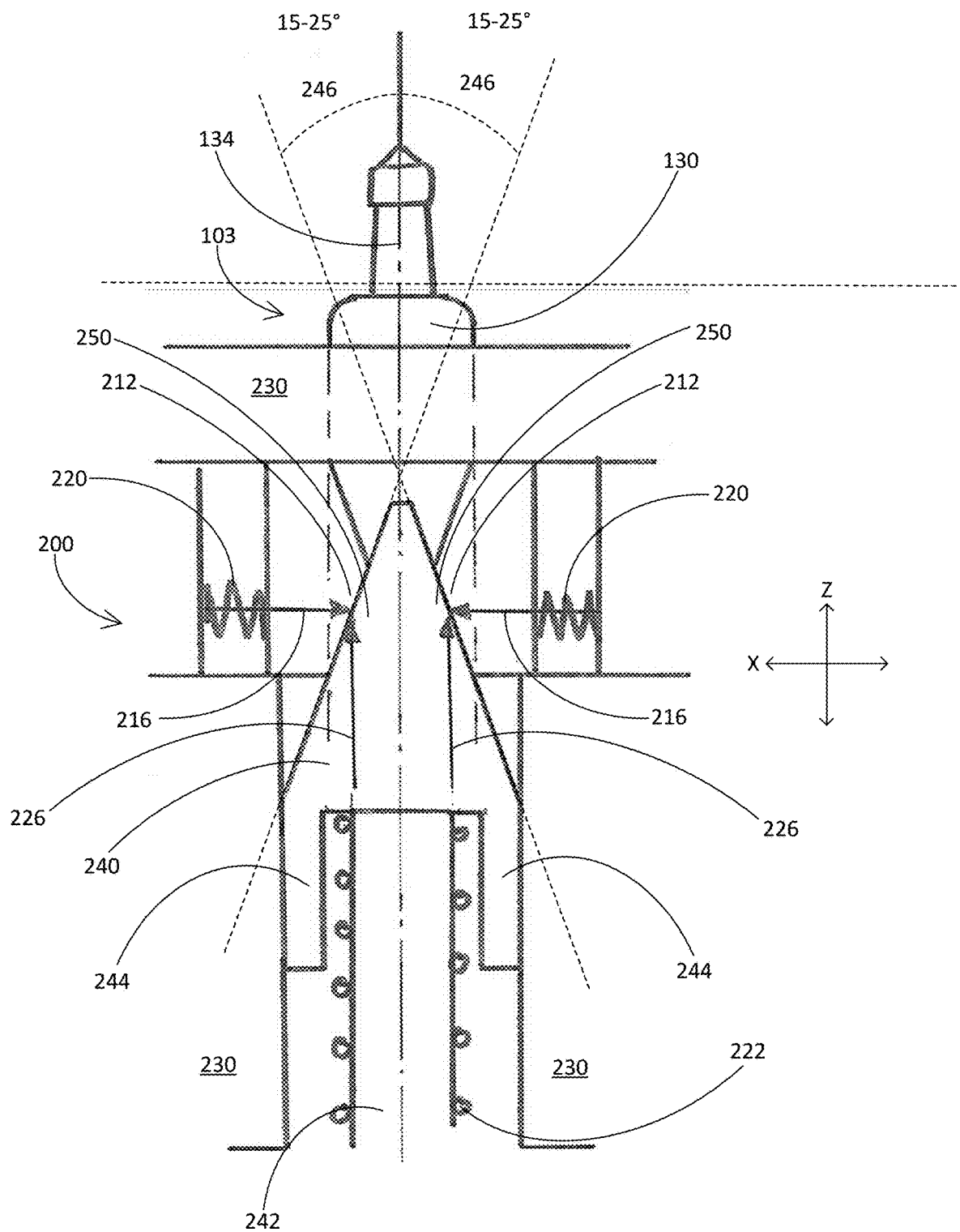
FIG. 4B is a schematic view of FIG. 4A.
Figure 5A:
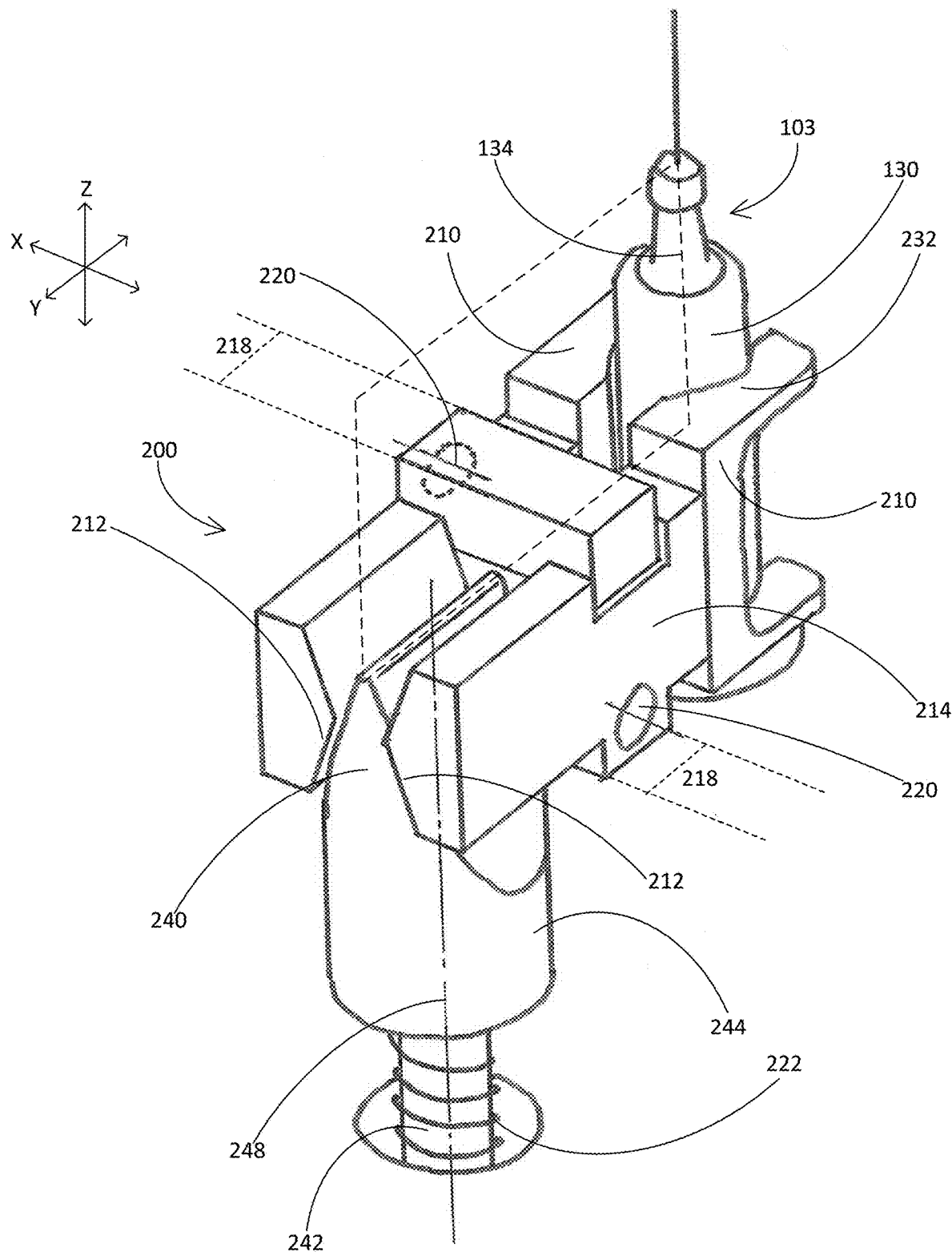
FIG. 5A is a perspective back view of the embodiment of FIG. 4A.
Figure 5B:
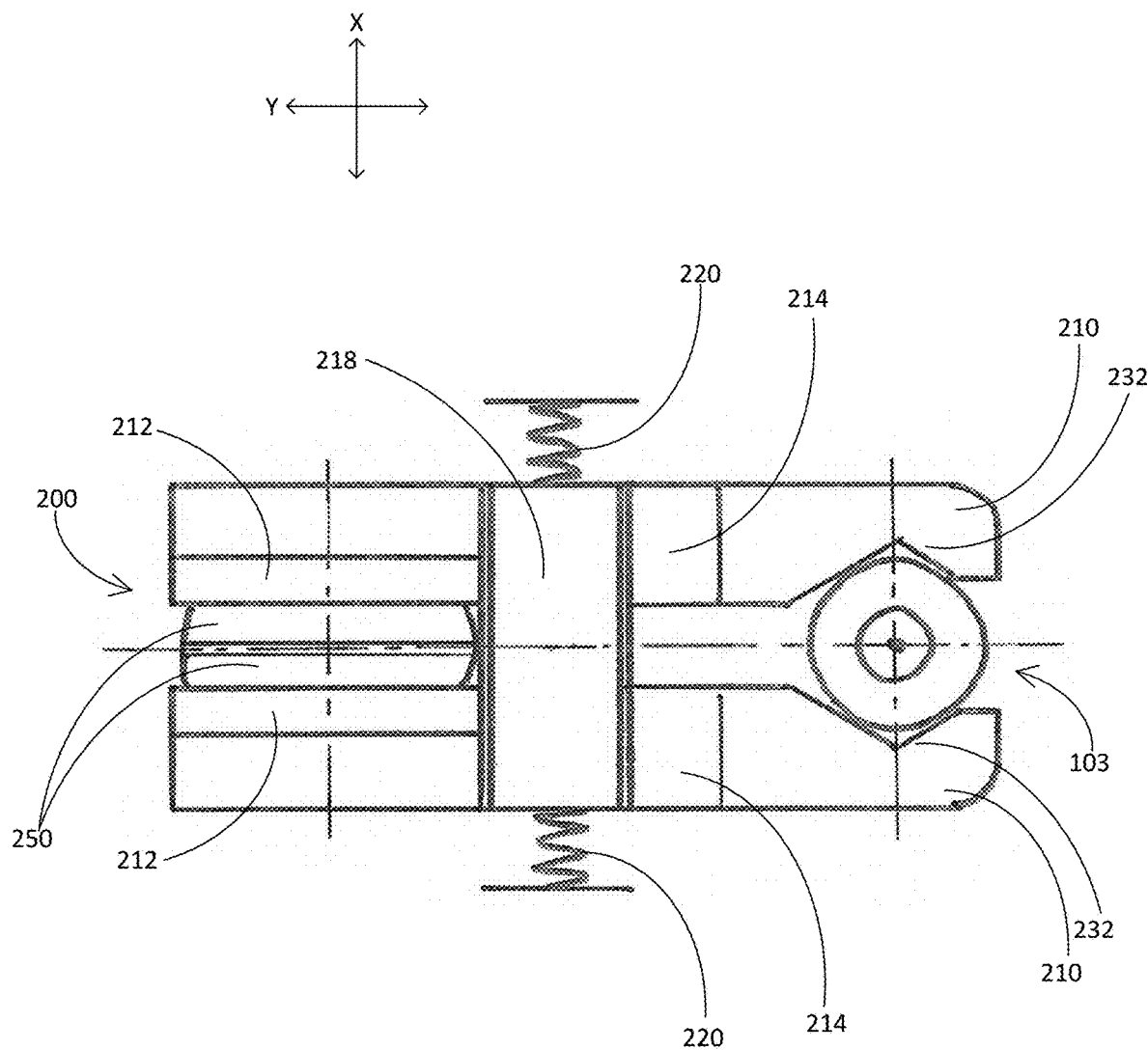
FIG. 5B is a top view of the embodiment of FIG. 4A.
Figure 5C:
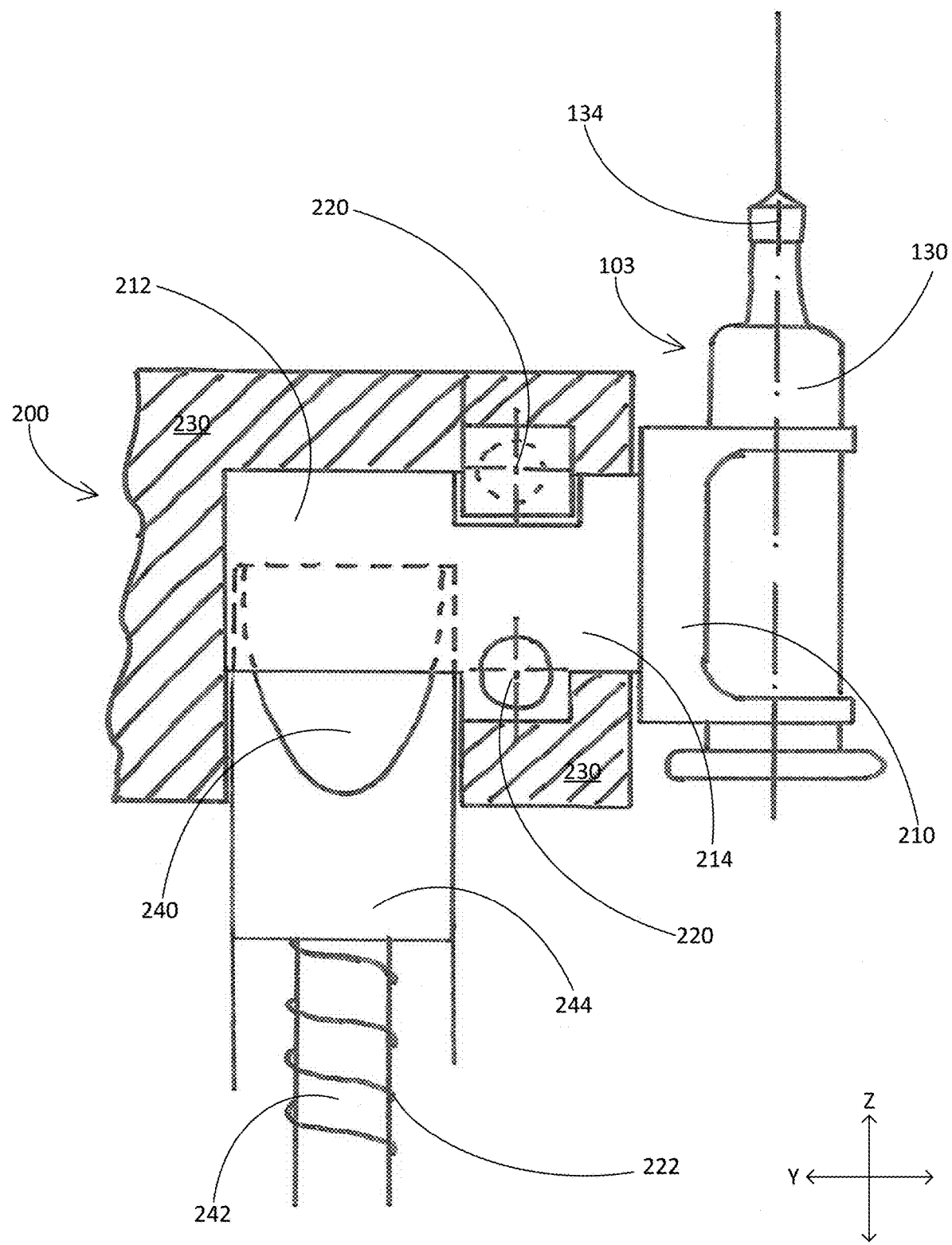
FIG. 5C is a cutaway side view of the embodiment of FIG. 4A.

FIG. 4A is a cutaway rear view of the system 200 according to an embodiment herein. FIG. 4B is a schematic view of FIG. 4A. FIG. 5A is a perspective back view of the embodiment of FIG. 4A. FIG. 5B is a top view of the embodiment of FIG. 4A. FIG. 5C is a cutaway side view of the embodiment of FIG. 4A. As shown in FIGS. 5A, 5B, and 5C, each of the pair of gripping arms includes a connecting portion 214 having a first end and a second end opposite the first end, a gripping arm 210 positioned at the first end, and a driven surface 212 positioned at the second end in a path of and oriented parallel to a corresponding driving surface 250 of the driving wedge 240. In other words, each driven surface 212 is complementary to a driving surface 250.

The system 200 includes a driving wedge 240 mounted in the housing 230 and slidable in the first (Z) direction (up and down in FIGS. 4A and 4B). The first direction is aligned with a first plane (Y-Z) passing through the part alignment position. While the first direction is parallel to the cylinder axis 134 in the present embodiment, a skilled person with the benefit of the present disclosure will appreciate that the first direction may be oriented at an angle or be perpendicular to the cylinder axis. In alternative embodiments, the driving wedge 240 may be an inverted wedge with the gripping arms adapted accordingly, e.g. to maintain a complementary relationship between driving and driven surfaces. The driving wedge 240 includes two driving surfaces 250. Each driving surface 250 has a driving angle 246 relative to the first direction, where the driving angle may be between 5 and 25 degrees. The driving surfaces 250 are positioned symmetrically with respect to the first direction, in this case having a mirror plane of symmetry passing through the first direction.

The system 200 may include an activating bolt 242 in some embodiments. The activating bolt 242 may transmit an activating force acting on the activating bolt to the wedge 240. The activating force may be provided mechanically, for example by a cam (not shown) pressing on activating bolt 242. In alternative embodiments, the activating force may be provided pneumatically, electrically, hydraulically or other known driving systems. The driving wedge 240 may be moved by the forces transmitted through activating bolt 242. In some embodiments, the wedge 240 includes wedge guidance portions 244 which engage the housing 230 to guide the wedge 240 as the wedge 240 slides in the first direction. The wedge 240 is biased away from the gripping arms 210 in the first direction by spring 222. In alternative embodiments, the wedge 240 may be biased towards the gripping arms 210, or may not be biased.

As shown in FIGS. 5A and 5B, the two gripping arms 210 are positioned such that contact between the driving surfaces 250 and the driven surfaces 212 causes the gripping arms 210 to move in at least the second direction an equal distance relative to the part alignment position in response to movement of the driving wedge 240 in the first direction. In particular, each gripping arm 210 includes a driven surface 212 oriented parallel to and positioned in the path of a corresponding driving surface 250. In other words, each gripping arm 210 includes a driven surface 212 complementary to a driving surface 250. Contact between each driven surface 212 and the corresponding driving surface 250 as the driving wedge 240 moves in an upward direction as shown in FIGS. 4A and 4B causes each driving surface 250 to exert a driving force 226 on each driven surface 212. Each driving force 226 contains a component parallel to the second direction, and if this component is greater than the biasing force 216 then the corresponding gripping arm 210 will slide in response to the force. Since each driving surface 250 is symmetrical around the Z direction, and the Z direction is aligned with the part alignment position, the movement of the two gripping arms 210 is symmetrical around the part alignment position. In other words, the two gripping arms 210 move an equal distance away from the part alignment position due to the movement of the wedge 240.

The gripping arms 210 include an additional driven surface positioned and oriented to be symmetrical with the driven surface 250 across a mirror plane of symmetry perpendicular to the first direction. In other words, the additional driven surface is symmetrical with the driven surface 250 to allow the gripping arms 210 to be reversible. Each gripping arm 210 may be rotated 180 degrees to be exchanged with each other gripping arm 210. This may extend the useable life of each gripping arm 210 by allowing a worn driven surface to be exchanged for an unworn additional driven surface.

In some embodiments, each gripping arm 210 comprises a guiding portion 218 and an opening having a shape and position to interface with a respective guiding portion 218 of the other gripping arms. Each guiding portion is configured to be slideably mountable in each respective guiding portion. Each guiding portion 218 guides each gripping arm 210 to provide more parallel movement of the two gripping arms 210.

The two gripping arms 210 are positioned equidistant in the second direction from the part alignment position and biased in opposite directions in the second (X) direction. In the present embodiment, the two gripping arms 210 are biased together, however a skilled person having the benefit of the present disclosure will appreciate that in alternative embodiments the two gripping arms 210 may be biased apart, with appropriate modifications in the driving wedge. In this embodiment, the two gripping arms 210 are biased by springs 220. In alternative embodiments, the two gripping arms 210 may be biased via electrical, hydraulic, pneumatic or other actuators or the like, however springs do not require a power supply to be connected to gripper arms 210 to function.

Generally speaking, the two gripping arms 210 cooperate to form two sets of self-centering jaws 232 positioned to align a gripped part with the part alignment position in a third direction, where the third direction is perpendicular to the second direction. In this embodiment, the two gripping arms 210 include a U-shaped end effector, include a first (sometimes "upper") and second (sometimes "lower") jaw 232, and cooperate to form a first and second set of jaws 232.

Figure 6:
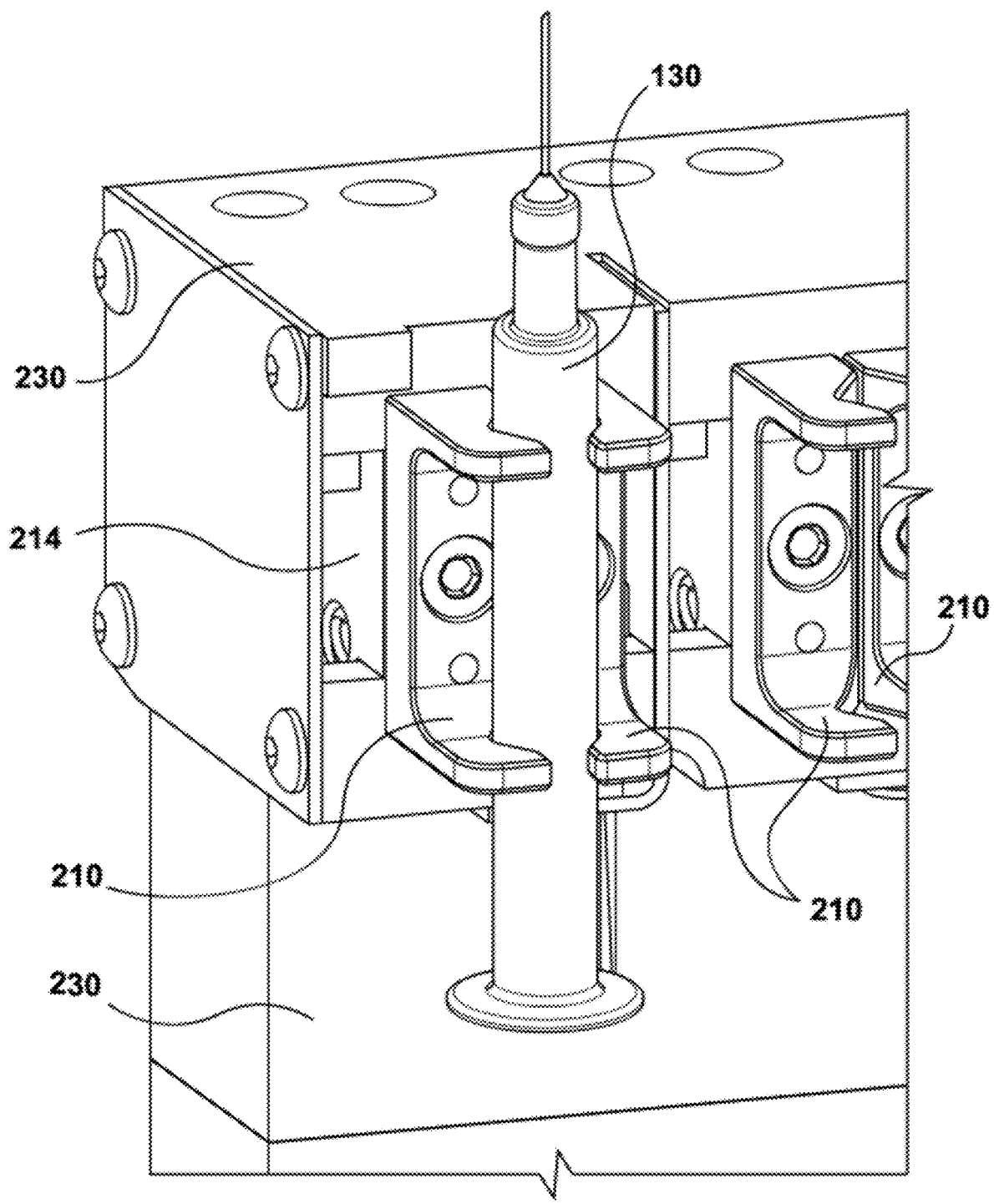
FIG. 6 is a perspective front view of a gripper holding a cylindrical body according to an embodiment herein.
Figure 7:
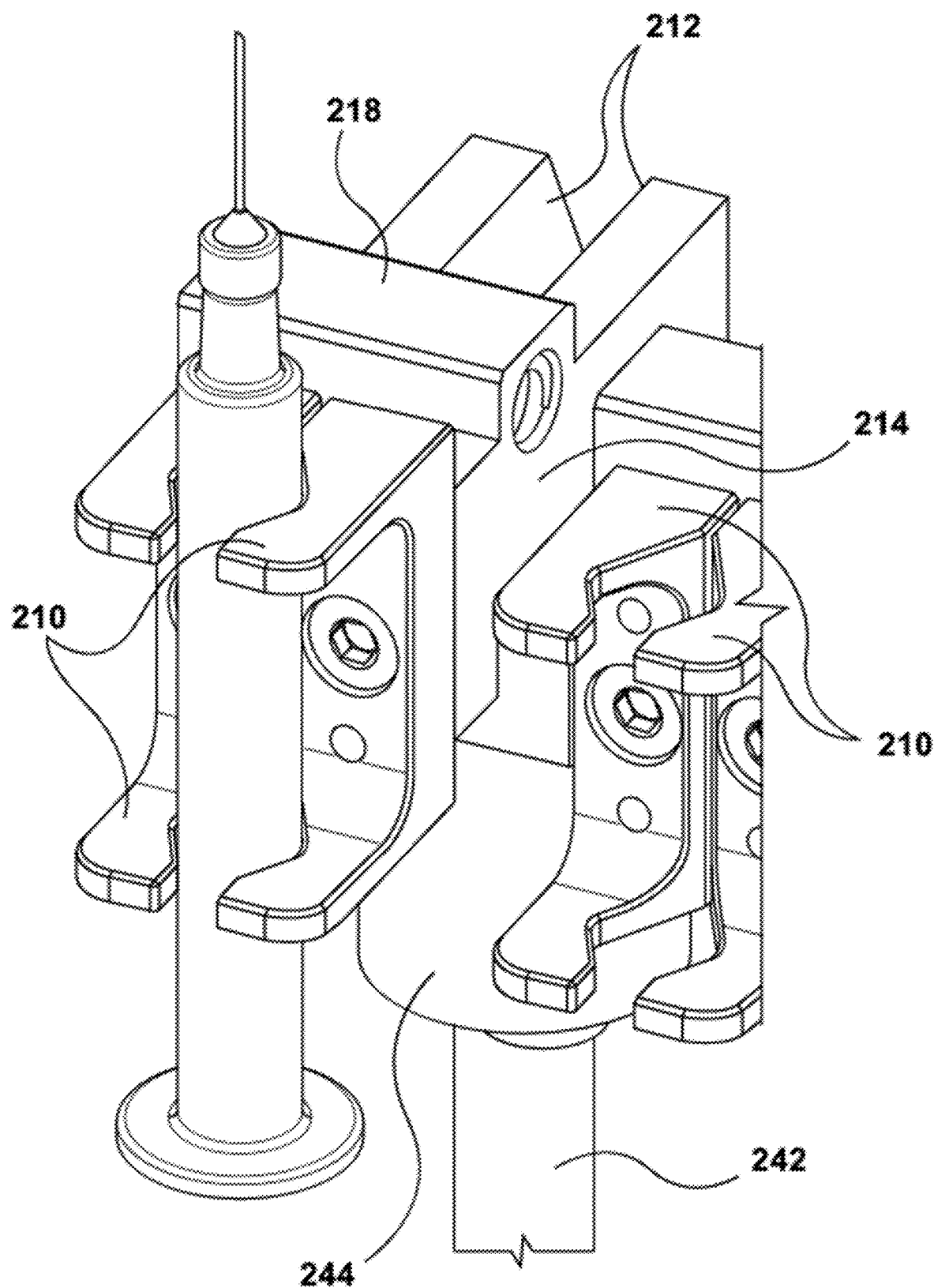
FIG. 7 is a perspective front exploded view of the gripper of FIG. 6 with the housing removed.
Figure 8:
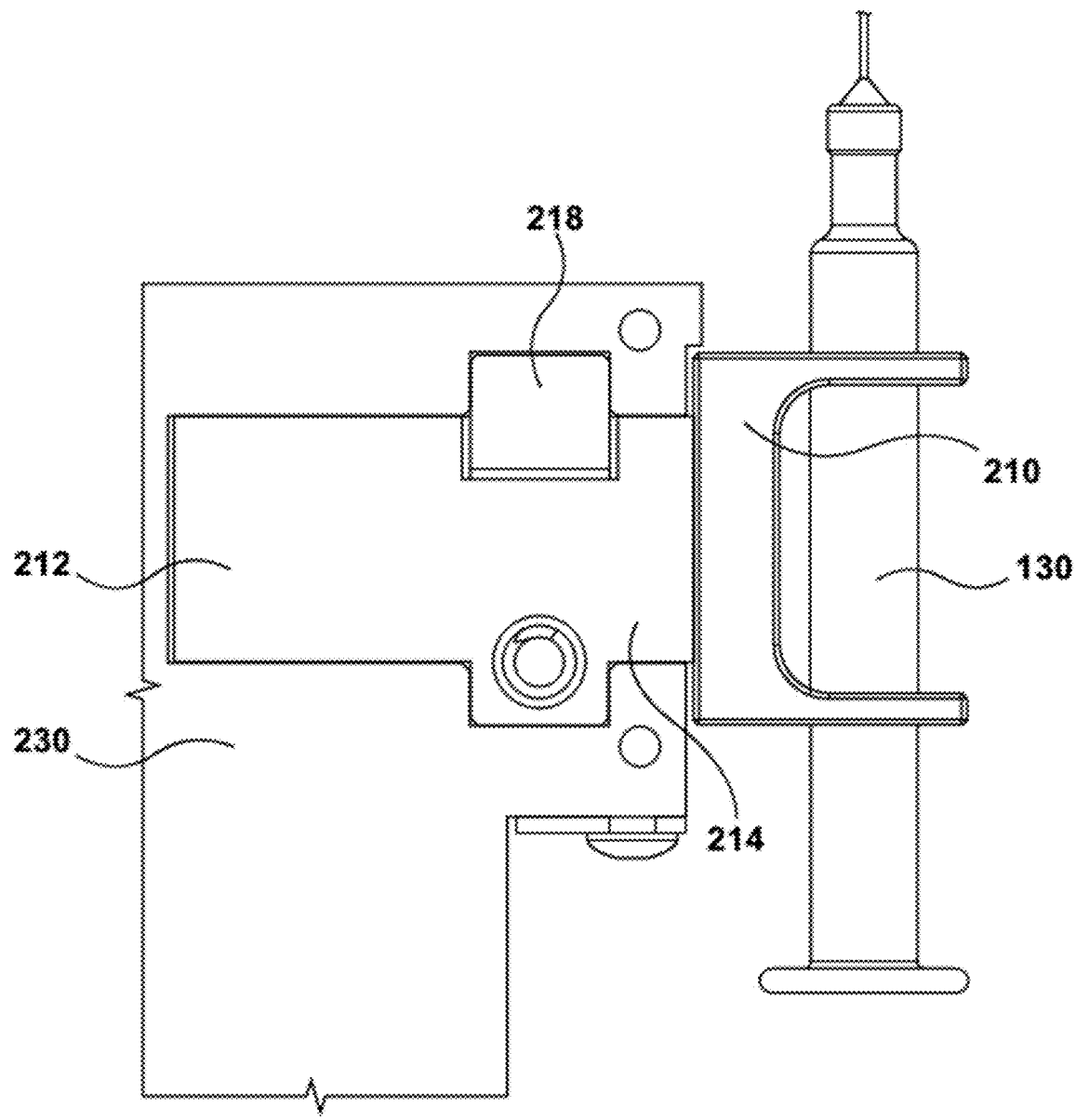
FIG. 8 is a side view of the gripper of FIG. 6.
Figure 9:
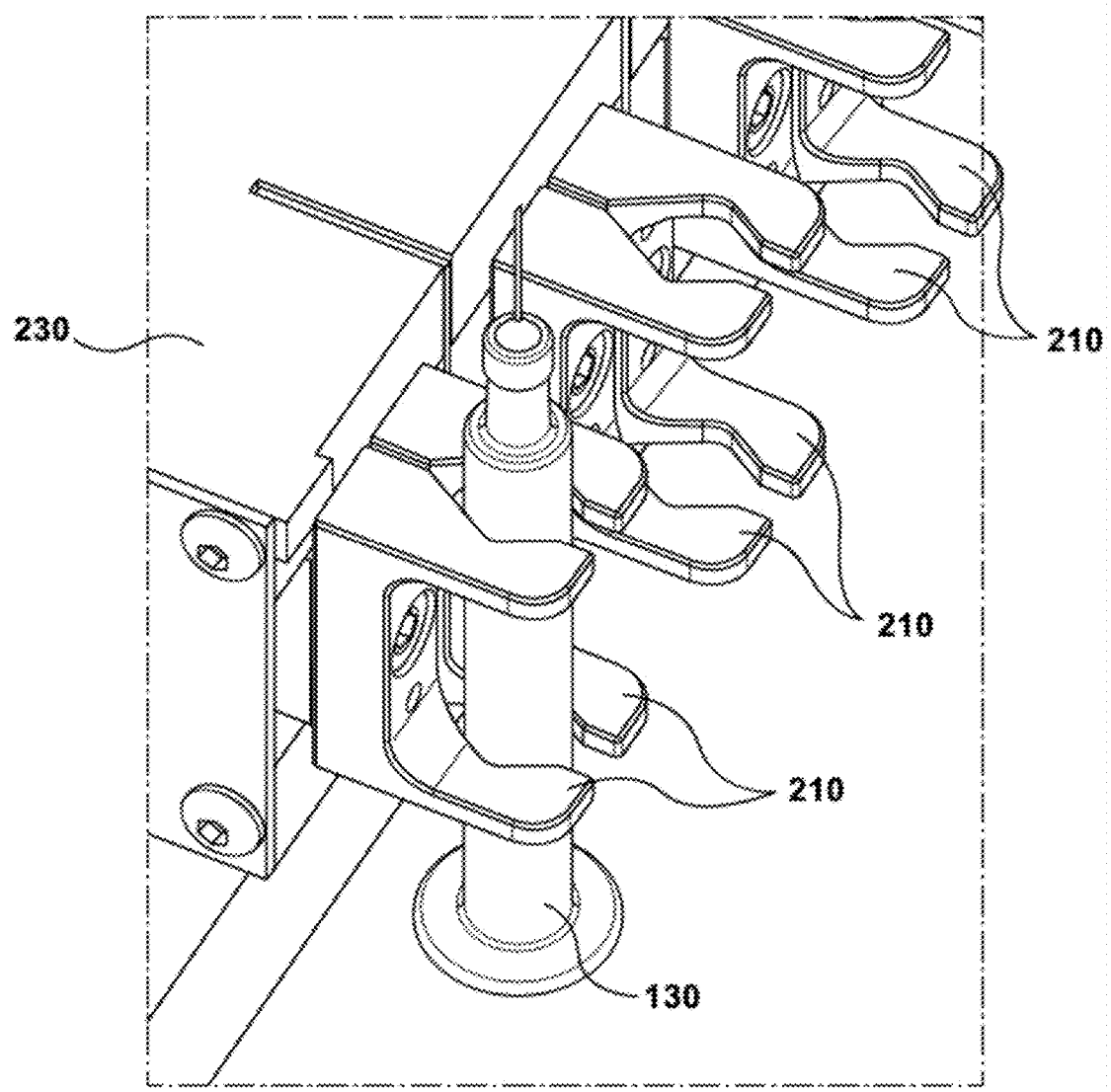
FIG. 9 is a perspective front view of the gripper of FIG. 6.
Figure 10:
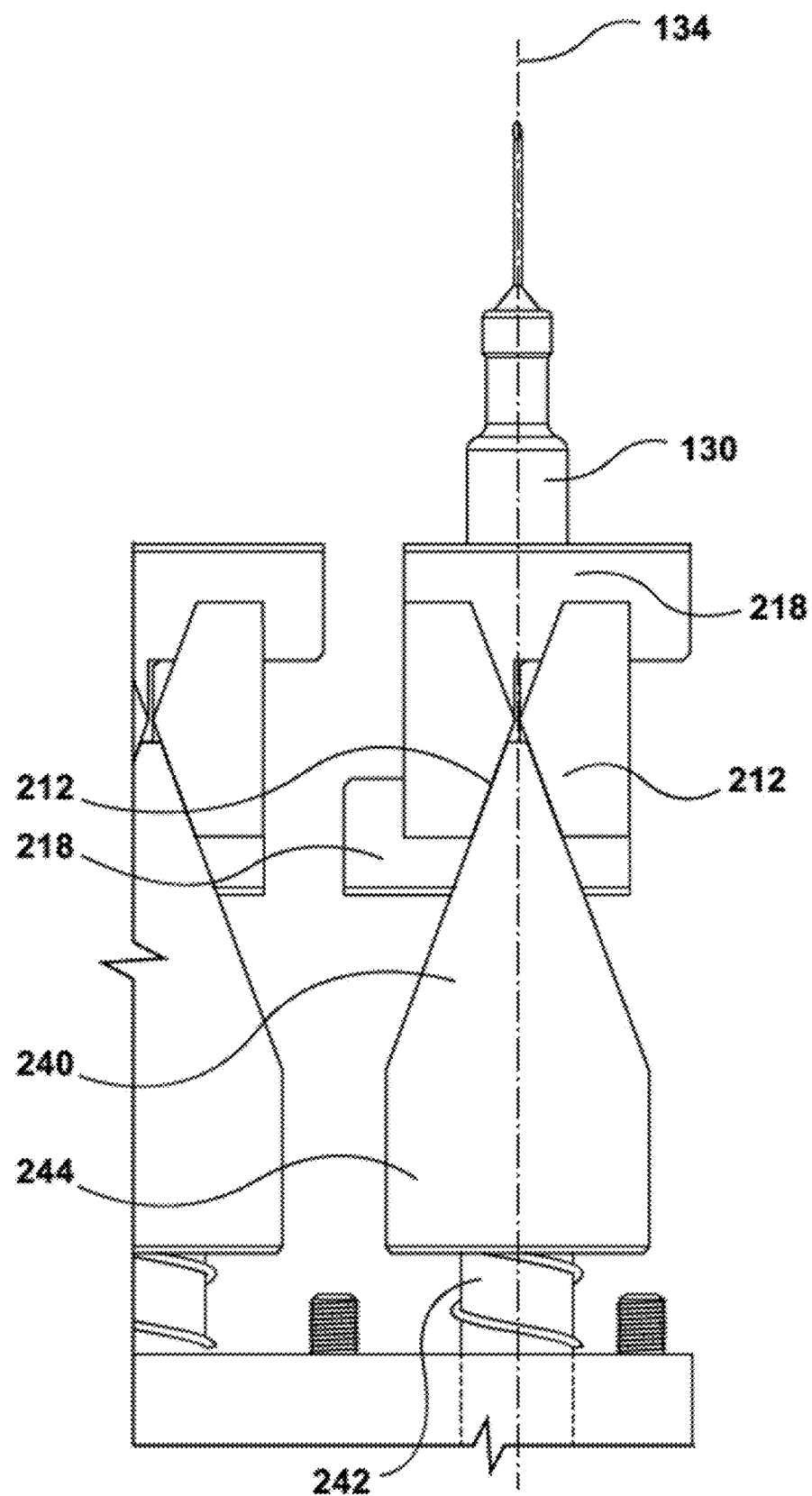
FIG. 10 is a back view of the gripper of FIG. 6 with the housing removed.
Figure 11:
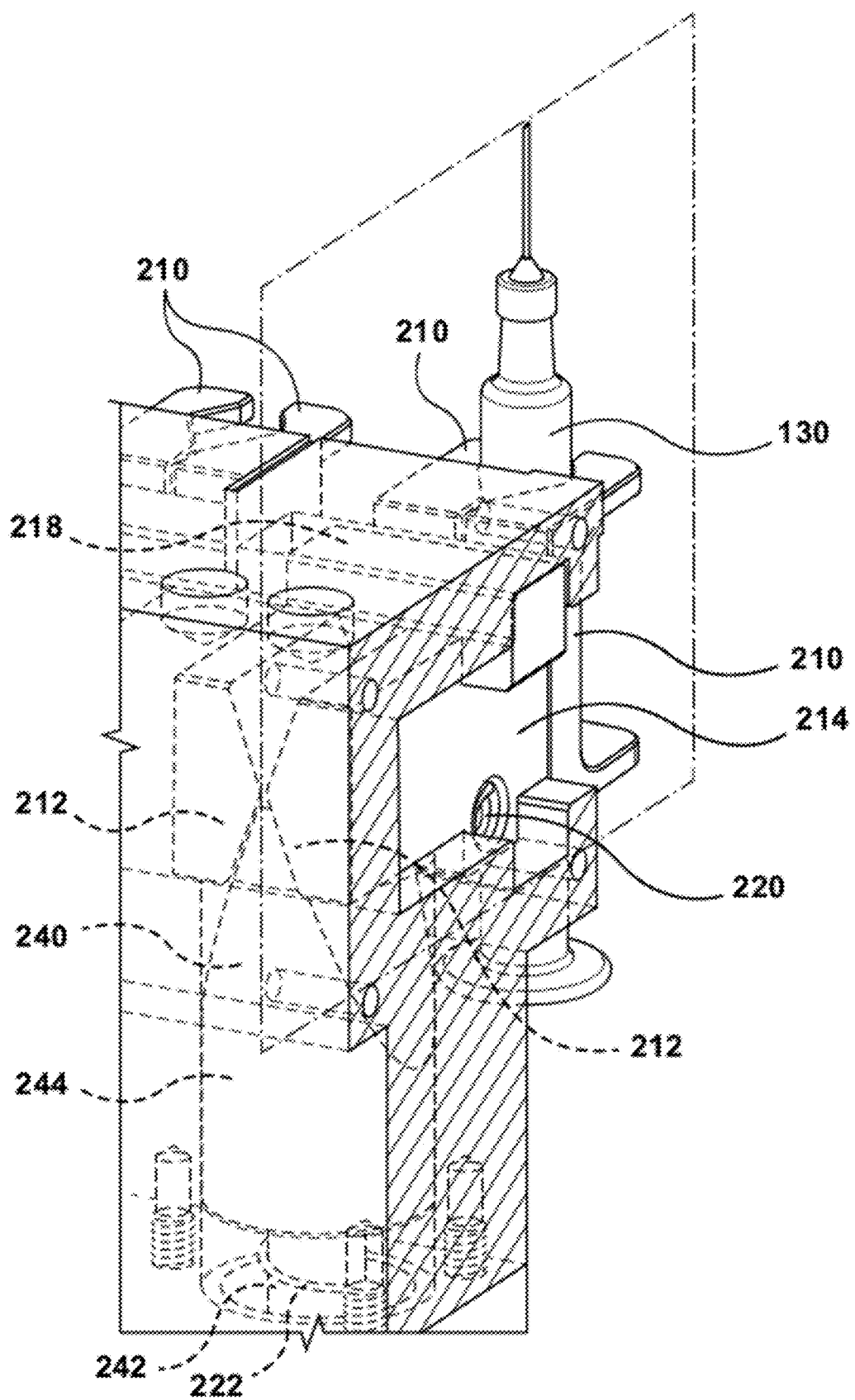
FIG. 11 is a perspective back view of the gripper of FIG. 6 with the housing shaded.

FIG. 6 is a perspective front view of another embodiment of a system 300. Similar parts in this embodiment will generally make use of similar reference numbers to the embodiment above. The system 300 includes a housing 230, a plurality of sets of gripping arms 210, and a plurality of wedges 240. As above, each set of gripping arms 210 and each corresponding driving wedge 240 is mounted in the housing 230, and each set of gripping arms 210 may hold a cylindrical body such as a syringe barrel. In this embodiment, each set of gripping arms 210 includes two gripping arms 210. FIG. 7 is a perspective front view of the gripper of FIG. 6 with the housing removed to better show the gripping arms 210. FIG. 8 is a side view of the gripper of FIG. 6. FIG. 9 is a perspective front view of the gripper of FIG. 6. FIG. 10 is a back view of the gripper of FIG. 6 with the housing removed. FIG. 11 is a perspective back view of the gripper of FIG. 6 with the housing shaded. As shown most clearly in FIG. 9, each set of gripping arms 210 is mounted adjacent to at least one other set of gripping arms 210, and multiple cylindrical bodies may be held simultaneously by the system 300.

A skilled person will appreciate that, while the present embodiment includes three sets of gripping arms 210 and three driving wedges 240, in alternative embodiments the gripper may include two, four, five, six or more sets of gripping arms 210 with corresponding driving wedges 240. In some embodiments, each set of gripping arms 210 with corresponding driving wedge 240 beyond the first may be referred to as an additional gripping arm and additional driving wedge. Each driving wedge 240 of the present embodiment may be activated concurrently by a single input. For example, a single cam may act on three wedges 240 (or three activating bolts 242) to move the wedges up and down to release and grip, respectively, three cylindrical bodies. Because each set of gripping arms 210 moves symmetrically, cylindrical bodies of differing sizes may be gripped in each of the three sets of gripping arms 210 while maintaining alignment with the respective part alignment positions of each set of gripping arms 210. In particular, as each driving wedge 240 moves downwards, each set of gripping arms 210 stops moving towards the part alignment position when contact is made with a cylindrical body. Since each driving wedge 240 and set of gripping arms 210 move independently, a given set of gripping arms 210 may stop moving without affecting the movement of neighbouring sets of gripping arms 210, which allows syringe barrels of different diameters to be gripped simultaneously by the system 300.

Figure 12:
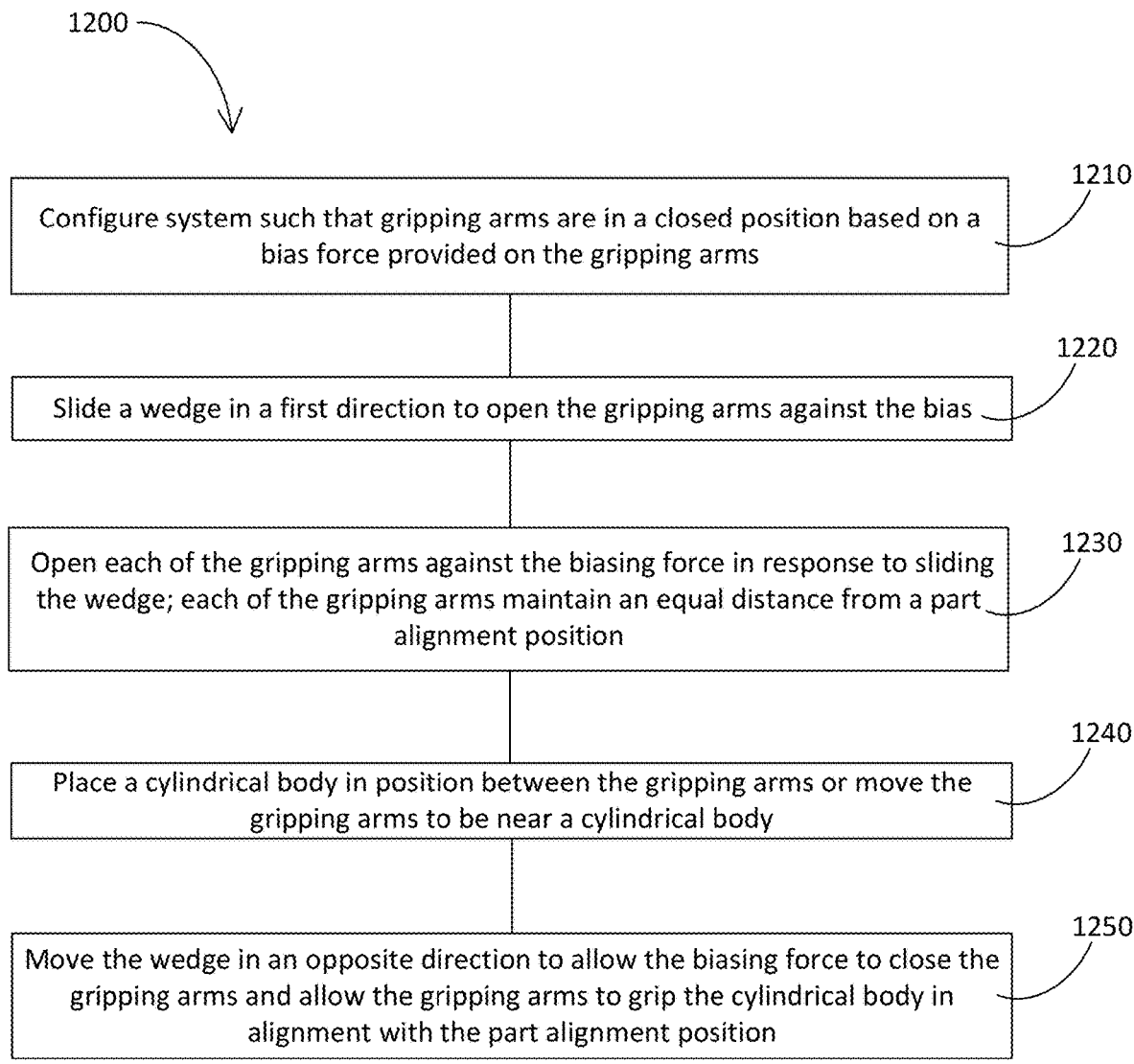
FIG. 12 is a flow diagram for a method for gripping a cylindrical object in a manufacturing environment.

FIG. 12 is a flow diagram for a method 1200 for gripping a cylindrical object in a manufacturing environment. A skilled person having the benefit of the present disclosure will appreciate that the method may be modified to provide other embodiments. Non-exclusive examples of physical elements that may be employed by method 1200 are called out in parentheses.

At 1210, a system (200, 300) is configured to have a plurality of gripping arms (210) biased into a closed position. In the closed position, the gripping arms (210) define a central plane therebetween.

At 1220, a wedge (240) is slid in a first direction that is parallel with the central plane. The wedge (240) and gripping arms (210) are configured to interact such that sliding the wedge (240) in the first direction causes the plurality of gripping arms (210) to open against the bias. In particular, each of the gripping arms (210) may include a driven surface (212) and the wedge (240) may include corresponding driving surfaces (250) that make contact in response to sliding the wedge (240) in the first direction and, thus, open the gripping arms (210). A skilled person having the benefit of the present disclosure will appreciate that the wedge (240) may also be slid in a different way but still achieve the intended result.

At 1230, the plurality of gripping arms (210) are opened against the biasing force (216) in response to sliding the wedge (240) in the first direction. Each of the plurality of gripping arms (210) is moved parallel to one another to generally maintain an equal distance between each portion of each gripping arm (210) and the central plane (sometimes called a part alignment position). Sliding the wedge (240) in the first direction exerts a wedge force greater than the biasing force (216) on the gripping arms (210) via contact between the wedge (240) and the plurality of gripping arms (210).

At 1240, a cylindrical body (110, 120, 130) is placed into the area of the gripping arms (210) or the gripping arms (210) are placed around or near the cylindrical body (110, 120, 130).

At 1250, the wedge (240) is removed (i.e. moved in the opposite direction) to allow the gripping arms (210) to grip the cylindrical body (110, 120, 130) in alignment with the central plane/part alignment position. In particular, as the wedge (240) is removed, the biasing force (216) is exerted against the cylindrical body (110, 120, 130) by each gripping arm (210) to grip the cylindrical body (110, 120, 130). In this way, the cylindrical body (110, 120, 130) is gripped in alignment with the part alignment position regardless of the diameter of the cylindrical body (110, 120, 130).

As described herein, the wedge (240) may include a plurality of driving surfaces (250). Each gripping arm (210) may include at least one driven surface (212) parallel to a corresponding one of the plurality of driving surfaces (250). Moving each gripping arm (210) in a second direction may include moving each portion of each gripping arm (210) in response to contact between each of the plurality of driven surfaces (212) and each corresponding driving surface (250).

In some embodiments, the method may further include: sliding the wedge (240) in the first direction again to cause movement of each of the plurality of gripping arms (210) against the biasing force (216) to allow the gripping arms (210) to release the cylindrical body (110, 120, 130) and thereby allow a new cylindrical body (110, 120, 130) to be gripped by the gripping arms.

It will be understood that a manufacturing process may be performed on the syringe barrel (110, 120, 130) when held in position by the gripper. For example, a needle (116, 126, 136) may be placed in each syringe barrel (110, 120, 130) (at the part alignment position) and glued in place as a part of the manufacture of syringes (101, 102, 103).

Figures 13A, 13B:
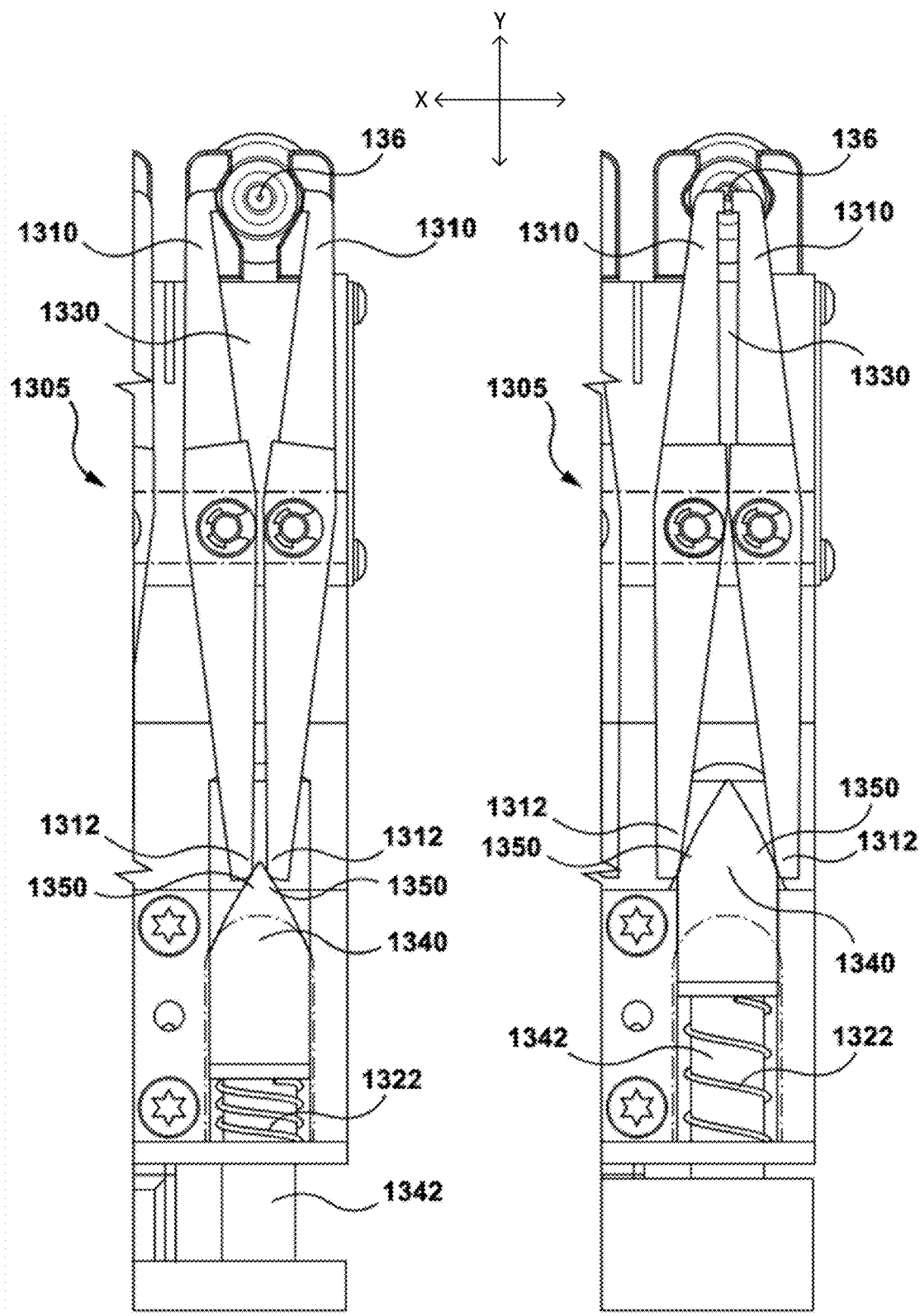
FIG. 13A is a top view of a system for gripping a cylindrical object according to an embodiment herein.
FIG. 13B is a top view of the system of FIG. 13A.
Figure 13C:
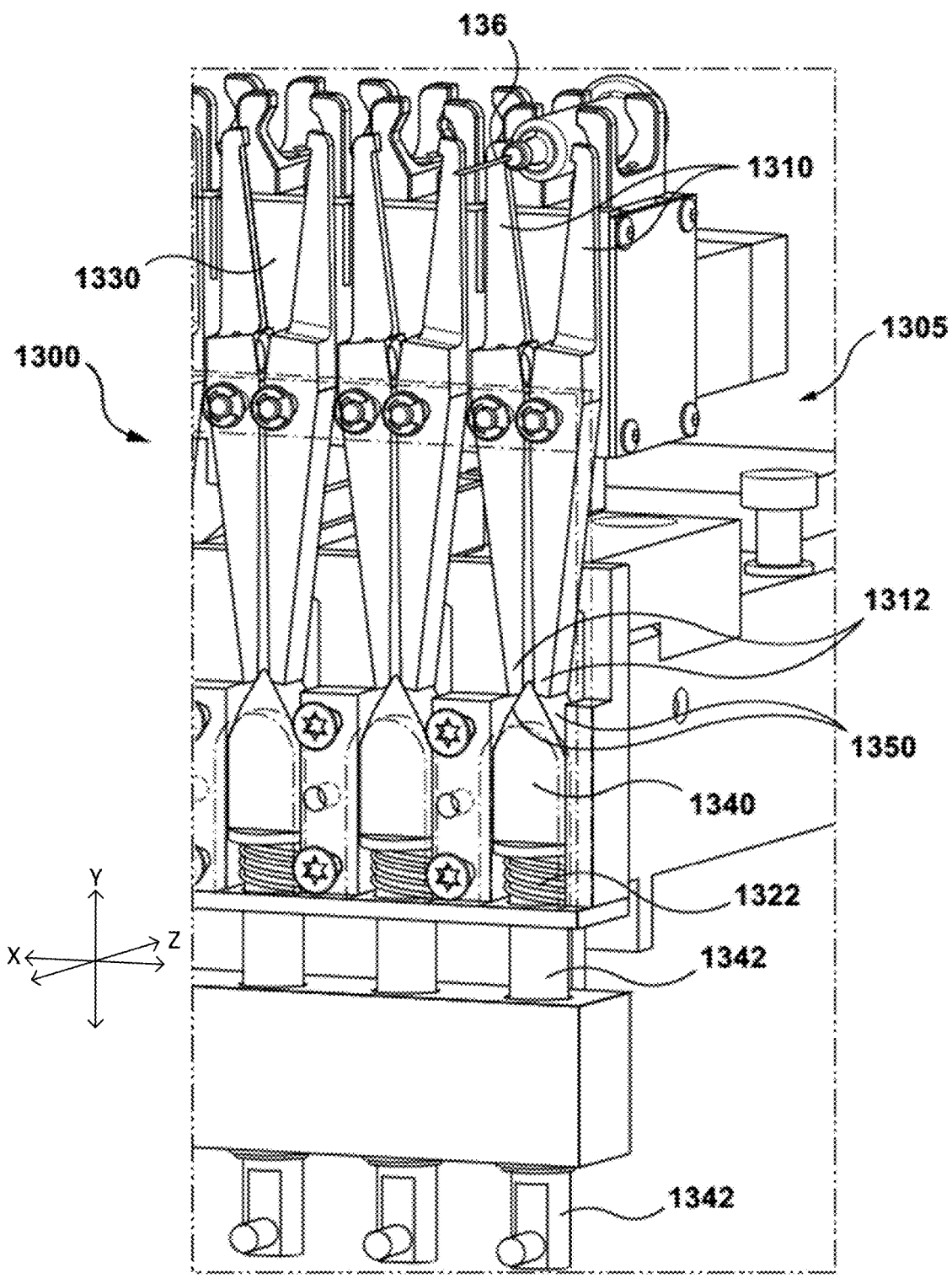
FIG. 13C is a perspective top view of the system of FIG. 13A.
Figure 13D:
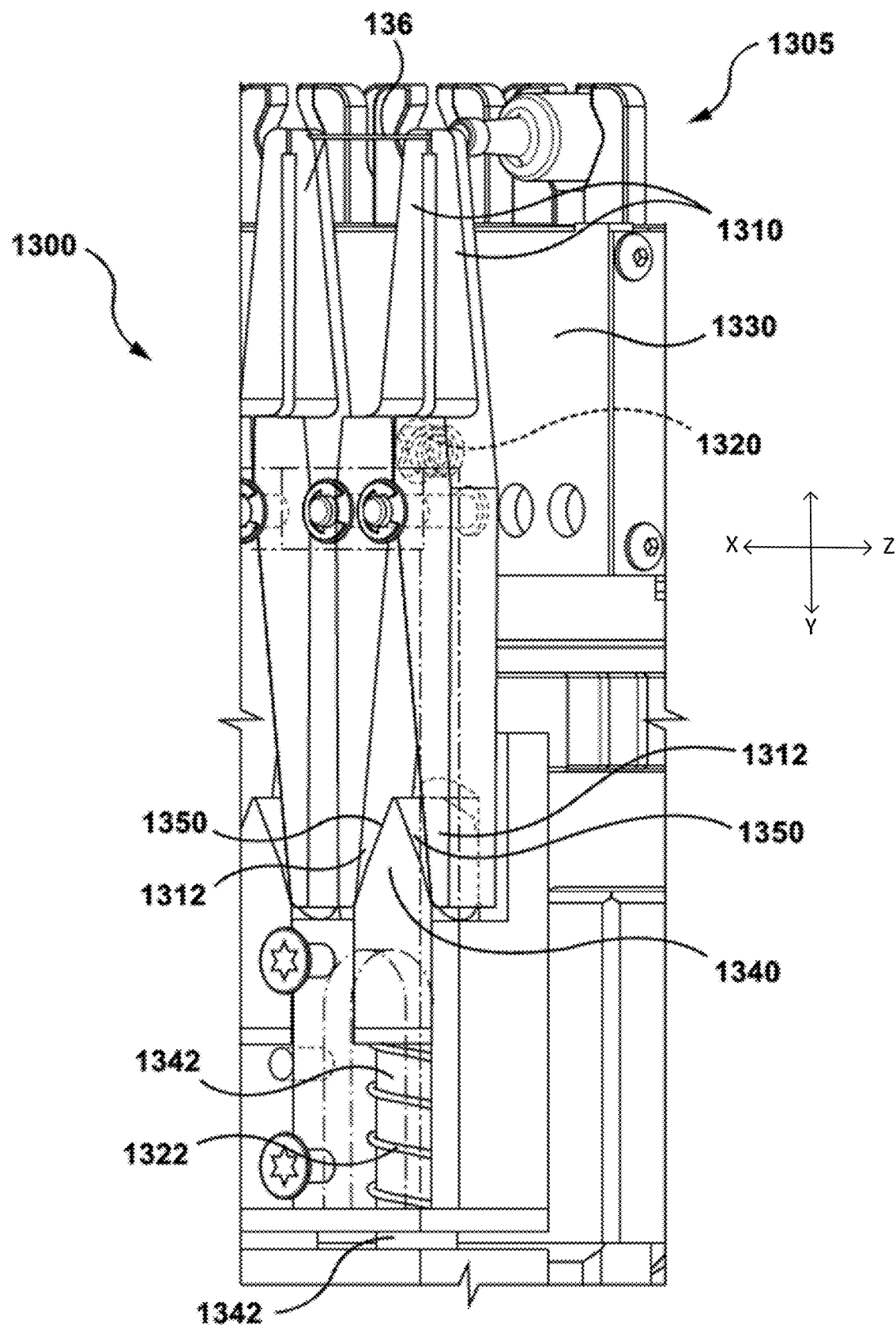
FIG. 13D is a perspective top view of the system of FIG. 13A.

FIG. 13A is a top view of a system 1300 in which a gripper 1305 is biased open and may be actuated to grip a cylindrical body, in this case a needle, cannula or the like, according to an embodiment herein. FIG. 13B is a top view of the system 1300 in which the gripper 1305 is actuated to grip a cylindrical body. FIG. 13C is a perspective top view of the system 1300. In this view, the gripper 1305 is shown biased open. FIG. 13D is a perspective top view of the system 1300 in which the gripper 1305 is actuated to grip a cylindrical body. The system 1300 includes the gripper 1305 (two gripping arms 1310, a spring 1320), a housing 1330, and a driving wedge 1340. The system 1300 is similar in some ways to the system 200 but has an opposite bias.

The driving wedge 1340 is mounted in the housing 1330 and is slidable in a first direction (referred to as the Y direction in the present embodiment). Each gripping arm 1310 is pivotably mounted in the housing 1330 and is pivotable around an axis perpendicular to the Y direction (referred to as the Z direction in the present embodiment). Pivoting each gripping arm 1310 causes at least a portion of each gripping arm 1310 to move at least partially in a third direction (referred to as the X direction in the present embodiment). The two gripping arms 1310 may be moved together to grip a cylindrical body and/or moved apart to release a cylindrical body. In particular, movement of each gripping arm 1310 in the X direction may cause the two gripping arms 1310 to grip and/or release a cylindrical body, for example a cannula or needle 136.

Each gripping arm 1310 includes a driven surface 1312. The driving wedge 1340 includes two driving surfaces 1350. The driving wedge 1340 is biased by spring 1322 and may be moved in response to forces exerted on an activating bolt 1342. The spring 1320 exerts a bias force on each gripping arm 1310, causing each gripping arm to be biased to an open position. The two gripping arms 1310 are positioned such that contact between the driving surfaces 1350 and the driven surfaces of the gripping arms 1310 causes the gripping arms 1310 to pivot in response to movement of the driving wedge 1340 in the first direction. In other words, movement of the driving wedge 1340 causes the two gripping arms 1310 to grip and/or release a cylindrical body in a manner similar in some ways to the operation of the system 200.

A skilled person having the benefit of the present disclosure will appreciate that the embodiments disclosed herein may be employed in an automated assembly system further including a system, such as a pick-and-place system, to position a cylindrical body (including positioning the cylindrical body in the Z direction) at a predetermined position or positions, a pallet to support the systems or parts disclosed herein, and a transport system to transport the pallet to and from at least one workstation. In particular, a system for assembling a syringe may include a first station for loading syringe barrels, a second station for loading cannulas/needles, a third station for positioning the cannulas/needles and syringe barrels in relation to each other, a fourth station (which may be combined with the third station), at which adhesive or the like is applied to hold the cannulas/needles in place, and a fifth station where the assembled syringe barrel and cannula/needle are released for further processing.

In the preceding description, for purposes of explanation, numerous details are set forth in order to provide a thorough understanding of the example embodiments. However, it will be apparent to one skilled in the art that these specific details may not be required. In other instances, well-known structures may be shown in block diagram form in order not to obscure the understanding. It will be further understood that, where appropriate, aspects from one embodiment may be used in other embodiments.

What has been described is merely illustrative of the application of some embodiments. It will be understood that elements of each embodiment may be combined with elements of other embodiments and that not every element in an embodiment is required. For example, each embodiment may include more or fewer elements as would be understood by one of skill in the art on reading this description. Further, other systems, apparatus and methods can be implemented by those skilled in the art without departing from the spirit and scope of the invention, which is defined by the following claims.

We claim:

1. A system for gripping a cylindrical object, the system comprising:
a housing;
a plurality of gripping arms provided to the housing, the plurality of gripping arms arranged in pairs with one gripping arm on an opposite side of a centerline plane from another gripping arm;
a driving wedge mounted in the housing and configured such that movement of the driving wedge moves each pair of gripping arms towards or away from each other such that each of the pair of gripping arms remains equidistant from the centerline plane; and a cam configured to move the driving wedge in relation to the plurality of gripping arms and the driving wedge is biased opposite to a direction in which the cam moves the driving wedge in relation to the plurality of gripping arms.

2. A system according to claim 1, wherein each of the plurality of gripping arms is biased toward the centerline plane and the driving wedge is configured to move each pair of gripping arms away from the centerline plane.

3. A system according to claim 1, wherein each of the plurality of gripping arms is biased away from the centerline plane and the driving wedge is configured to move each pair of gripping arms toward the centerline plane.

4. A system according to claim 1, wherein each of the plurality of gripping arms comprises a driven surface and the driving wedge comprises at least one driving surface configured to match with the driven surface to move the gripping arm.

5. A system according to claim 4, wherein each of the plurality of gripping arms comprises: a connecting portion having a first end and a second end opposite the first end; a gripping portion positioned at the first end; and the driven surface positioned at the second end.

6. A system according to claim 4, wherein each of the plurality of gripping arms comprises an additional driven surface symmetrical with the first driven surface across a mirror plane of symmetry perpendicular to the first direction.

7. A system according to claim 4, wherein each driven surface and driving surface are configured at complementary driving angles with respect to the centerline plane.

8. A system according to claim 7, wherein the driving angle is between 5 and 25 degrees.

9. A method for actuating a gripper for a cylindrical object, the method comprising:
configuring the gripper to be closed based on a biasing force on a plurality of gripping arms;
opening the plurality of gripping arms against the bias by using a cam to slide a wedge in a first direction to slide against a corresponding one of the plurality of gripping arms such that each of the gripping arms maintain an equal predetermined distance from a part alignment position;
placing a cylindrical body between the plurality of gripping arms; and
closing the plurality of gripping arms by biasing the wedge to slide in an opposite direction to allow the biasing force to close the gripping arms and allow the gripping arms to grip the cylindrical body in alignment with the part alignment position.

10. A method according to claim 9 wherein the wedge comprises at lease one driving surface and each gripping arm comprises at least one driven surface corresponding to the driving surface, and wherein opening the gripping arms comprises moving each gripping arm in response to contact between the driving surface and the corresponding driven surface.

11. A method according to claim 10, wherein the closing the gripping arms comprises moving each gripping arm in response to a reduced contact between the driving surface and the corresponding driven surface aided by the biasing force.

12. A method according to claim 9, further comprising opening the plurality of gripper arms to release the cylindrical body from the plurality of gripping arms.

13. A system for gripping a cylindrical object, the system comprising:
a housing;
a driving wedge mounted in the housing and slidable in a first direction (Z), the first direction (Z) aligned with a first plane (Y-Z) passing through a part alignment position, the driving wedge comprising a plurality of driving surfaces positioned symmetrically and at a driving angle relative to the first (Z) direction;
a plurality of gripping arms mounted in the housing and movable in at least a second (X) direction, each of the plurality of gripping arms including one of a plurality of driven surfaces complementary to one of the plurality of driving surfaces, each of the plurality of gripping arms positioned such that contact between the plurality of driving surfaces and the plurality of driven surfaces causes the plurality of gripping arms to move in at least the second (X) direction in response to movement of the driving wedge in the first direction; and
a cam configured to move the driving wedge in relation to the plurality of gripping arms and the driving wedge is biased opposite to a direction in which the cam moves the driving wedge in relation to the plurality of gripping arms.

14. A system according to claim 13, wherein the gripping system further comprises:
at least one additional driving wedge mounted in the housing and slidable in an additional first (Z) direction, the additional first direction (Z) aligned with an additional first plane (Y-Z) passing through an additional part alignment position, each additional driving wedge comprising an additional plurality of driving surfaces positioned symmetrically and at an additional driving angle relative to the additional first (Z) direction; and
at least one additional plurality of gripping arms mounted in the housing and movable in at least an additional second (X) direction, each of the additional plurality of gripping arms including one of an additional plurality of driven surfaces complementary to one of the additional plurality of driving surfaces, each of the additional plurality of gripping arms positioned such that contact between the additional plurality of driving surfaces and the additional plurality of driven surfaces causes the additional plurality of gripping arms to move in at least the additional second (X) direction in response to movement of the additional driving wedge in the additional first direction.

\* \* \* \* \*